United States Patent [19]
Lee et al.

[11] Patent Number: 5,132,322
[45] Date of Patent: Jul. 21, 1992

[54] ETOPOSIDE ANALOGUES

[75] Inventors: Kuo-Hsiung Lee; Zhe Oing Wang; J. Phillip Bowen, all of Chapel Hill, N.C.; Dora M. Schnur, St. Louis, Mo.; Yung-Chi Cheng, Woodbridge, Conn.; Su-Ying Liu, Belmont, Calif.; Yao H. Kuo, Taipei, China; Masami Mori, Aichi, Japan

[73] Assignee: The University of North Carolina at Chapel Hill, Chapel Hill, N.C.

[21] Appl. No.: 406,330

[22] Filed: Sep. 12, 1989

Related U.S. Application Data

[63] Continuation-in-part of Ser. No. 313,826, Feb. 23, 1989, abandoned.

[51] Int. Cl.$^5$ .................. A61K 31/36; A61K 31/365; C07D 307/77
[52] U.S. Cl. .................. 514/468; 514/463; 514/467; 549/298; 549/358; 549/432
[58] Field of Search .................. 549/298, 358, 432; 544/148; 546/174, 270; 514/232.5, 313, 338, 463, 467, 468

[56]      References Cited
U.S. PATENT DOCUMENTS
4,567,253  1/1986  Durst et al. .................. 549/298

FOREIGN PATENT DOCUMENTS
63-10789  1/1988  Japan .................. 549/298

Primary Examiner—C. Warren Ivy
Assistant Examiner—Ba K. Triny
Attorney, Agent, or Firm—Cushman, Darby & Cushman

[57] ABSTRACT

Compounds that are analogs of etoposide and exhibit antitumor activity are disclosed. The compounds of the present invention have the following formula:

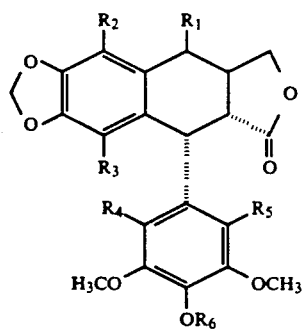

where:
$R_1$ is $\beta$-OCH$_2$CH$_2$NH$_2$, $\beta$-NHCH(CH$_3$)CH$_2$OH, $\beta$-NHCH$_2$CH(CH$_3$)OH, $\beta$-Cl, $\beta$-Br, $\beta$-OH, $\alpha$-OH, $\beta$-NH, $\alpha$-NH$_2$, $\beta$-NHCH$_2$CH$_2$OH, $\alpha$-NHCH$_2$CH$_2$OH, $\beta$-NHCH$_2$CH$_2$CH$_3$, $\beta$-NHCH$_2$CH$_2$OCH$_3$, $\beta$-NHCH$_2$CH=CH$_2$, $\beta$-NHCH$_2$CH(OH)CH$_3$, $\beta$-NHCH$_2$CH$_2$CH$_2$OH, $\beta$-OCH$_2$CH$_2$OH,

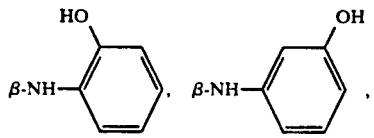

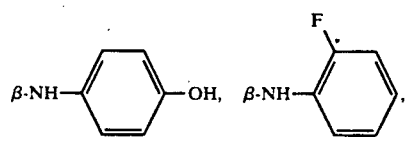

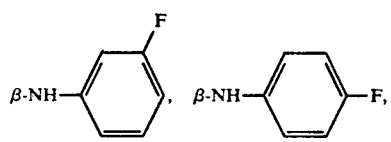

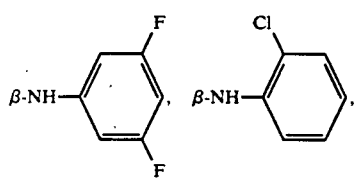

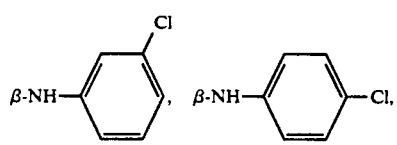

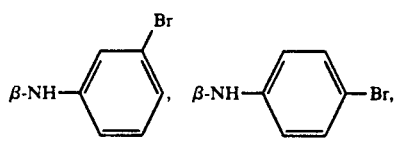

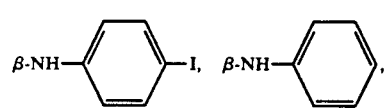

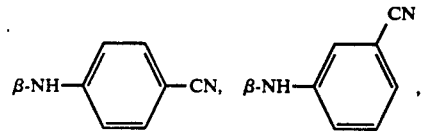

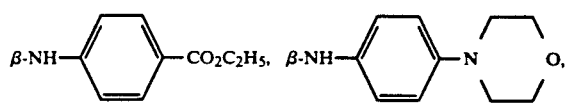

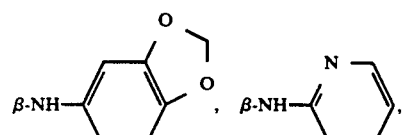

(Abstract continued on next page.)

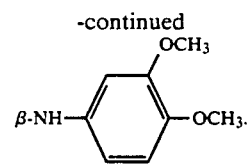
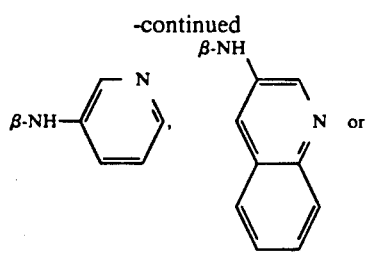
$R_2$ is H, or Br;
$R_1$ is H, or Br;
$R_4$ is H, or Br;
$R_5$ is H, or Br; and
$R_6$ is H, or —$CH_3$.
9 Claims, No Drawings

ETOPOSIDE ANALOGUES

This invention relates to compounds that are analogs of etoposide having antitumor activity. This invention also relates to a method for treating tumors by administering a safe and effective amount of the etoposide analog compounds.

BACKGROUND OF THE INVENTION

Podophyllotoxin is a naturally occurring compound extracted from the mandrake plant. Recently two therapeutically useful semi-synthetic glycosides of podopyllotoxin, etoposide (also known as VP-16), shown below, and teniposide (also known as VM-26), have been developed.

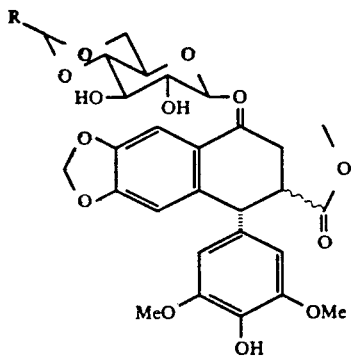

R = CH₃ (Etoposide)

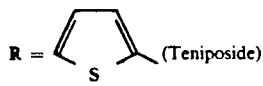

(Teniposide)

These compounds exhibit therapeutic activity in several human neoplasms, including small cell carcinomas of the lung, testicular tumors, Hodgkin's disease, Papillomavirus, and diffuse histiocytic lymphoma.

It is believed that these drugs block the catalystic activity of DNA topoisomerase II by stabilizing an enzyme-DNA complex in which the DNA is cleaved and covalently linked to the enzyme. See Chen, G. L., Yang, L., Rowe T. C., Halligan, B. D., Tewey, K., and Liu, L., *J. Biol. Chem.*, 259, 13560 (1984); Ross, W., Rowe, T., Glisson, B., Yalowich, J., and Liu, L., *Cancer Res.*, 44, 5857 (1984); Rowe, T., Kuppfer, G., and Ross, W., *Biochem. Pharmacol.*, 34, 2483 (1985), which are all herein specifically incorporated by reference. By way of background, topoisomerases are enzymes which control the topological state of DNA. Type II topoisomerases catalyze DNA strand passage through transient double strand breaks in the DNA. The resulting change in the linking number of DNA allows these enzymes to mediate DNA interconversions, such as supercoiling and relaxation of supercoiling, catenation and decatenation, knotting, and unknotting. See Wang, J. C., *Annu. Rev. Biochem.*, 54, 665 (1985) and Maxwell, A., and Gellert, M., *Adv. Protein Chem.*, 38, 69 (1986), which are herein specifically incorporated by reference.

Type II DNA topoisomerase enzymes have been shown to be involved in a number of vital cellular processes, including DNA replication and transcription, and chromosomal segregation. These enzymes, therefore, are a critical target for the action of a wide variety of anticancer drugs, including etoposide and teniposide. The key step leading to cell death may be the capability of these drugs to block the catalytic activity of DNA topoisomerase II, as noted above.

Structure-activity studies have demonstrated a direct correlation between cytotoxicity, DNA breakage, and murine-derived topoisomerase II inhibition activities among the podophyllotoxin analogues. See Minocha, A., and Long, B., *Biochem Res. Comm.*, 122, 165 (1984), which is herein specifically incorporated by reference. The isolation and purification of human type II topoisomerase from lymphocytic leukemia cells has provided the means to use this enzyme as a target to investigate the structure-activity relationships among etoposide and related congeners.

It has been shown that the substitution of etoposide's glycosidic moiety by an 4-alkoxy group, as in 4'-demethyl-epipodophyllotoxin ethyl ether, preserves the inhibitory activity of DNA topoisomerase II intact at higher concentrations. See Thurston, L. S., Irie, H., Tani, S., Han, F. S., Liu, Z. C., Cheng, Y. C., and Lee, K. H., *J. Med. Chem.*, 29, 1547 (1986), which is herein specifically incorporated by reference. However, it has also been shown that a series of 4-acyl congeners are less active, even though some of them possessed potent cytotoxicity. See Thurston, L. S., Imakura, Y., Haruna, M., Li, D. H., Liu, Z. C., Liu, S. Y., Cheng, Y. C., and Lee, K. H., *J. Med. Chem.*, 31, (1988), which is herein specifically incorporated by reference.

SUMMARY OF THE INVENTION

The present invention provides novel compounds which exhibit antitumor activity. The compounds are analogs of etoposide. More specifically, preferred compounds of the present invention are etoposide analogs wherein the glycosidic moiety is replaced by various substituents, such as a 2''-hydroxyethylamino chain, a 2''-methoxyethylamino chain, a 4''-fluoroanilinyl chain, a chlorine atom, or a bromine atom. present invention. The compounds of the present invention have been shown to inhibit type II human topoisomerase and also to cause cellular protein-linked DNA breakage and, therefore, may be useful in the treatment of tumors. The compounds may also be useful in the treatment of papilloma virus.

In accordance with the present invention, there are provided compounds of the formula:

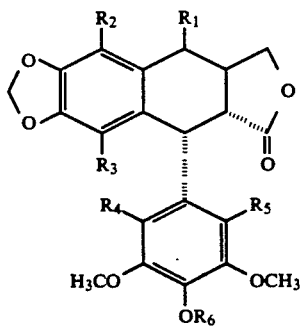

wherein
$R_1$ is β-OCH₂CH₂NH₂, β-NHCH(CH₃)CH₂OH, β-NHCH₂CH(CH₃)OH, β-Cl, β-Br, β-OH, α-OH, β-NH₂, α-NH₂, β-NHCH₂CH₂OH, α-NHCH₂CH₂OH, β-NHCH₂CH₂CH₃, β-NHCH₂CH₂OCH₃, β-

NHCH$_2$CH=CH$_2$, β-NHCH$_2$CH(OH)CH$_3$, β-NHCH$_2$CH$_2$CH$_2$OH, β-OCH$_2$CH$_2$OH,

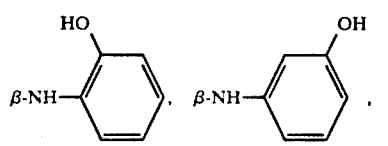

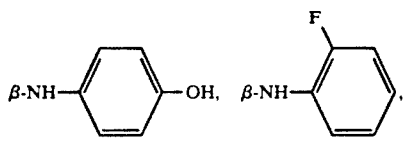

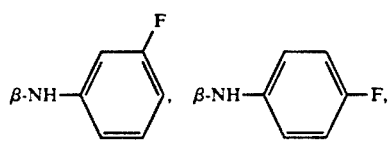

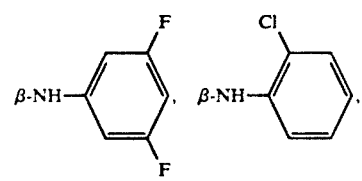

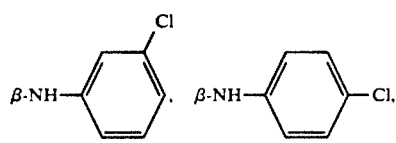

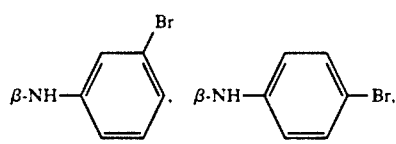

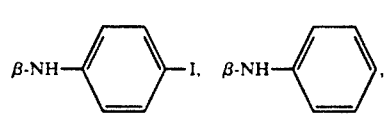

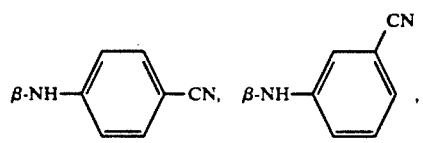

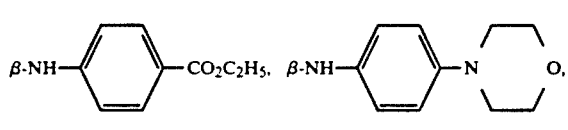

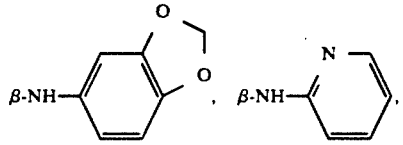

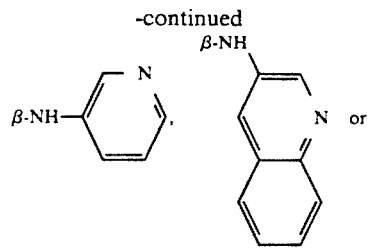

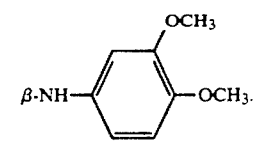

R$_2$ is H, or Br;
R$_3$ is H, or Br;
R$_4$ is H, or Br;
R$_5$ is H, or Br; and
R$_6$ is H, or —CH$_3$.

The present invention is also for a process for treating tumors in humans and lower animals by administering a safe and effective amount of a compound as described above.

A preferred group of compounds within the present invention exhibit inhibitory activity on human type II DNA topoisomerase to an equal or greater extend than etoposide and are of the formula:

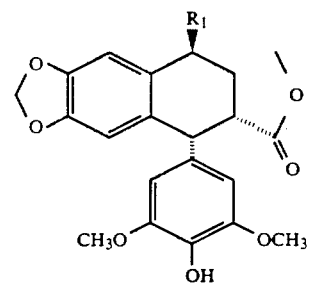

wherein
R$_1$ is —NHCH$_2$CH$_2$OH, —NHCH$_2$CH$_2$OCH$_3$, NHCH$_2$CH(OH)CH$_3$, NHCH(CH$_3$)CH$_2$OH, Cl, OCH$_2$CH$_2$NH$_2$.

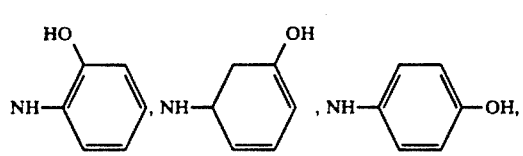

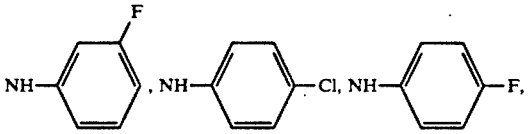

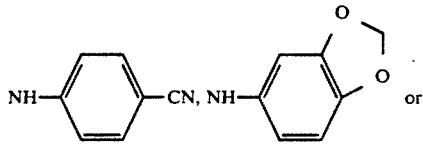

-continued

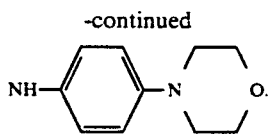

Particularly preferred compounds include 4'-Demethyl-4β-amino-4-desoxypodophyllotoxin; 4'-Demethyl-4β-[2''-hydroxyethylamino]-4-desoxypodophyllotoxin; 4'-Demethyl-4β-[2''-hydroxypropylamino]-4-desoxypodophyllotoxin; 4'-Demethyl-4β-[1''-methyl-2''-hydroxyethylamino]-4-desoxypodophyllotoxin; 4β-Chloro-4-desoxypodophyllotoxin; 4'-demethyl-4β-Chloro-4-desoxypodophyllotoxin; 4'-Demethyl-4β-[3''-hydroxyanilinyl]-4-desoxypodophyllotoxin; 4'-Demethyl-4β-[2''-hydroxyanilinyl]-4-desoxypodophyllotoxin; 4'-Demethyl-4β-[-4''-hydroxyanilinyl]-4-desoxypodophyllotoxin; 4'-Demethyl-4β-[2''-fluoroanilinyl]-4-desoxypodophyllotoxin; 4'-Demethyl-4β-[3''-fluoroanilinyl]-4-desoxypodophyllotoxin; 4'-Demethyl-4β-[4''-fluoroanilinyl]-4-desoxypodophyllotoxin; 4'-Demethyl-4β-[3'',5''-difluoroanilinyl]-4-desoxypodophyllotoxin; 4'-Demethyl-4β-[4''-chloroanilinyl]-4-desoxypodophyllotoxin; 4'-Demethyl-4β-[4''-bromoanilinyl]-4-desoxypodophyllotoxin; 4'-Demethyl-4β-anilinyl-4-desoxypodophyllotoxin; 4'-Demethyl-4β-[4''-cyanoanilinyl]-4-desocypodophyllotoxin; 4'-Demethyl-4β-[3''-cyanoanilinyl]-4-desoxypodophyllotoxin; 4'-Demethyl-4β-[4''-ethoxycarbonylanilinyl]-4-desoxypodophyllotoxin; 4'-Demethyl-4β-[4''-morpholinoanilinyl]-4-desoxypodophyllotoxin; 4'-Demethyl-4β-[3'',4''-methylenedioxyanilinyl]-4-desoxypodophyllotoxin; 4'-Demethyl-4β-[3'',4''-dimethoxyanilinyl]-4-desoxypodophyllotoxin; 4'-Demethyl-4β-[3''-pyridylamino]-4-desoxypodophyllotoxin; and 4'-Demethyl-4β-[3''-quinolonylamino]-4-desoxypodophyllotoxin.

Additional objects and advantages of the invention will be set forth in part in the description which follows, and in part will be obvious from the description, or may be learned from the practice of the invention.

DESCRIPTION OF THE PREFERRED EMBODIMENTS

Reference will now be made in detail to the presently preferred embodiments of the invention, which together with the following examples, serve to explain the principles of the invention.

As noted above, the present invention relates to compounds of the formula:

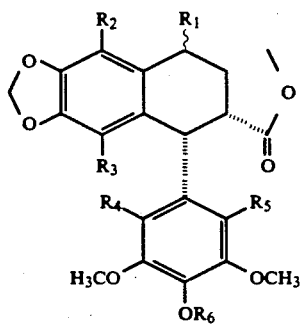

wherein
$R_1$ is β-OCH$_2$CH$_2$NH$_2$ β-NHCH(CH$_3$)CH$_2$OH, β-NHCH$_2$CH(CH$_3$)OH, β-Cl, β-Br, β-OH, α-OH, βNH$_2$, α-NH$_2$, α-NHCH$_2$CH$_2$OH, β-NHCH$_2$CH$_2$CH$_3$, β-NHCH$_2$CH$_2$OCH$_3$, β-NHCH$_2$CH=CH$_2$, β-NHCH$_2$CH(OH)CH$_3$, β-NHCH$_2$CH$_2$CH$_2$OH, or —OCH$_2$CH$_2$OH,

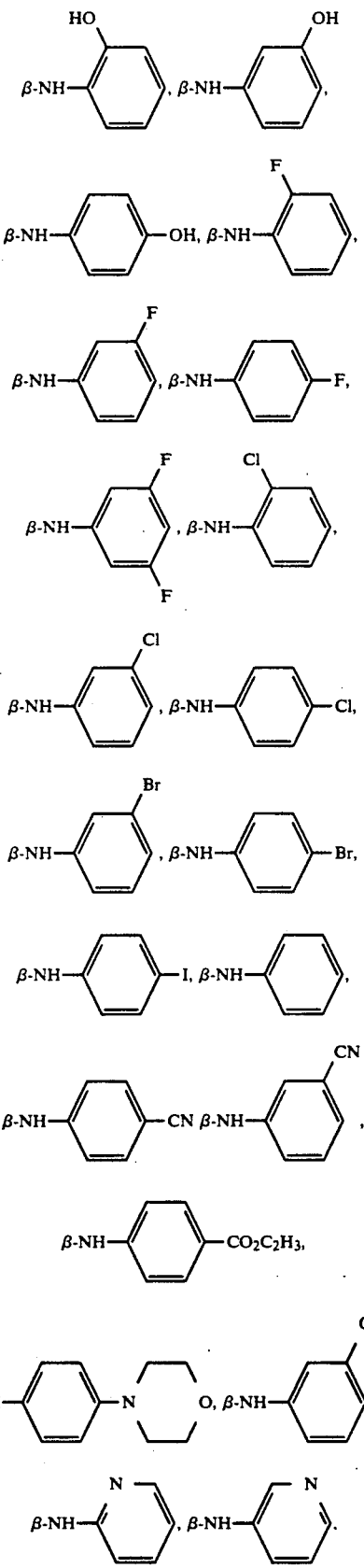

-continued

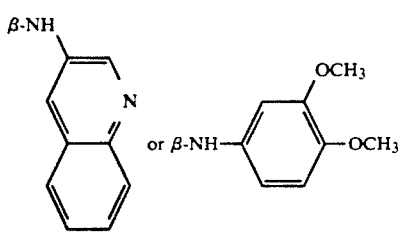

$R_2$ is H, or Br;
$R_3$ is H, or Br;
$R_4$ is H, or Br;
$R_5$ is H, or Br; and
$R_6$ is H, or —$CH_3$.

As noted above, a preferred group of compounds within the present invention exhibit inhibitory activity on human type II DNA topoisomerase to an equal or greater extend as etoposide and are of the formula:

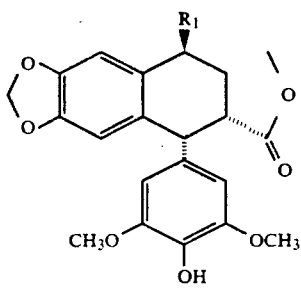

wherein
$R_1$ is $NHCH_2CH_2OH$, $NHCH_2CH_2OCH_3$, $NHCH_2CH(OH)CH_3$, $NHCH(CH_3)CH_2OH$, Cl, $OCH_2CH_2NH_2$,

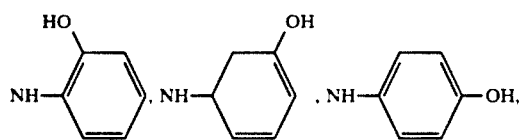

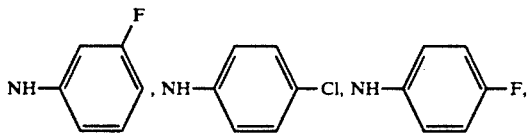

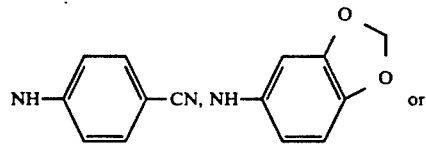

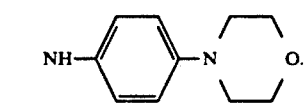

Another preferred group of compounds under the present invention will possess a 4′-demethyl-4β-substituted anilinyl 4-desoxypodophyllotoxin wherein the compound possesses the following formula.

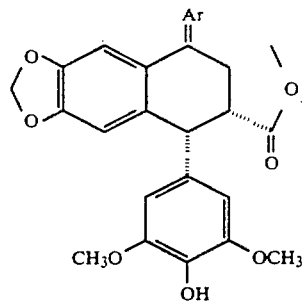

wherein Ar is an arylamine as in the formula below,

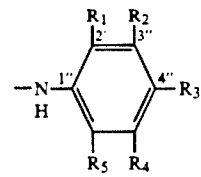

wherein
$R_1$ is H, OH, F, Cl, Br, $CO_2CH_3$, $CO_2C_2H_5$, CN, $NO_2$, $NH_2$, $N(CH_3)_2$, $OCH_3$, $CH_2OH$, $CH_3$, $CF_3$, $CH_2CH_2OH$, $COCH_3$, $CH_2NH_2$;

$R_2$ is H, OH, F, Cl, Br, $CO_2CH_3$, $CO_2C_2H_5$, CN, $NO_2$, $NH_2$, $N(CH_3)_2$, $OCH_3$, $CH_2OH$, $CH_3$, $CF_3$, $CH_2CH_2OH$, $COCH_3$, $CH_2NH_2$, $CHOHCH_3$, $SCH_3$, $CH_3$, $CO_2CH_3$;

$R_3$ is H, OH, F, Cl, Br, I, $CO_2CH_3$, $CO_2C_2H_5$, CN, $NO_2$, $NH_2$, $N(CH_3)_2$, $OCH_3$, $CH_2OH$, $CH_3$, $CF_3$, $CH_2CH_2OH$, $COCH_3$, $CH_2NH_2$,

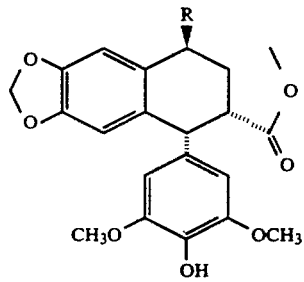

$N(CH_2CH_2OH)_2$, $CH_3$;
$R_4$ is H, F, Cl, OH, $OCH_3$, $CO_2CH_3$, $CO_2C_2H_5$, $CH_3$, $CF_3$, $NO_2$, $NH_2$, Cl;
$R_5$ is H, F, Cl, $CH_3$, $CF_3$, OH, $OCH_3$, $NO_2$; $R_3$ and $R_4$ are $OCH_2O$ or $OCH_2CH_2O$.

The preferred compounds of the present invention can also be more generally described as a compound of the formula:

wherein R is a flat aromatic group which may contain a heteroatom or alternatively may contain electron donating substituents at the 3″ or 4″ position of the aromatic ring. Specifically the substituents may be oxygen containing groups, or the aromatic group may be pyridine.

The compounds of the present invention are analogs of etoposide wherein the glycosidic moiety has been replaced. Compounds exhibiting potent inhibition of human DNA topoisomerase II result from replacing the glycosidic moiety with a 2″-hydroxyethylamino chain, a 2″-methoxyethylamino chain, or a substituted arylamine at the C-4β position. Inhibitory activity can also be increased by substituting the glycosidic moiety by chlorine, bromine, or an amino group at the C-4β position. It is believed that the stereochemistry of the 4β-substituents plays an important role in determining inhibitory potency. In general, β-isomers exhibit greater activity than the corresponding α-isomers. Another factor affecting the potency is the length of the substituent group at the C-4 position and the substitution on that group. This distance factor is different for halide and hydroxy substituted arylamines. For the hydroxy substituted arylamine, the meta position showed the most potency, while in the halogens, para substitution showed the most potency. A second potency factor regarding the halogen substituted aryl amines is the size of the halogen. Fluorine, the smallest has the most potency, while Iodine, the largest has the least. In addition, substitution of bromine at either one or more of the $R_2$, $R_3$, $R_4$, and $R_5$ positions will result in compounds having significant inhibitory activity. $R_6$ can be varied by substituting hydrogen with a methyl group. These modifications will produce changes in inhibitory activity which can be readily determined by assays known in the prior art through the exercise of routine skill in light of the teachings contained herein.

The compounds of the present invention were tested for their degree of inhibitory activity on human type II DNA topoisomerase, their effect on the formation of protein-linked DNA breakage, and their cytotoxicity. The inhibitory activity for compounds of the present invention correlated with the ability of the compounds to cause DNA strand breakage. However, the in vitro cytotoxicity of the compounds tested did not appear to correlate with the enzyme inhibitory activity and DNA strand break activity. The results of the tests on some of the compounds of the present invention are shown in Tables I and III. For a description of the assays used with respect to the compounds listed in Tables I and III see Thurston, L. S., Irie, H., Tani, S., Han, F. S., Liu, Z. C., Cheng, Y. C., and Lee, K. H., Antitumor Agents 78. Inhibition of Human DNA Topoisomerase II by Podophyllotoxin and α-Peltatin Analogues, *J. Med. Chem.* 29, 1547 (1986), and the references cited therein.

Tables I, and III illustrate the inhibitory activity, DNA strand breakage ability, as well as the cytotoxicity of etoposide and some of the compounds of the present invention. As shown in Tables I and III, the inhibitory activity of 4′-Demethyl-4β-amino-4-desoxypodophyllotoxin (Example 3), 4′-Demethyl-4β-[2″-hydroxyethylamino]-4-desoxypodophyllotoxin (Example 5), 4′-Demethyl-4β-[2″-hydroxypropylamino]-4-desoxypodophyllotoxin (Example 10), and 4′-Demethyl-4β-[1″-methyl-2″-hydroxyethylamino]-4-desoxypodophyllotoxin (Example 11), 4′-Demethyl-4β-[2″-aminoethoxy]4-desoxypodophyllotoxin (Example 13); 4′-Demethyl-4β-[3″-hydroxyanilinyl]-4-desoxypodophyllotoxin (Example 33), 4′-Demethyl-4β-[2″-hydroxyanilinyl]-4-desoxypodophyllotoxin (Example 34), 4′-Demethyl-4β-[4″-hydroxyanilinyl]-4-desoxypodophyllotoxin (Example 35), 4′-Demethyl-4β-[3″-fluoroanilinyl]-4-desoxypodophyllotoxin (Example 26); 4′-Demethyl-4β-[4″-fluoroanilinyl]-4-desoxypodophyllotoxin (Example 28); 4′-Demethyl-4β-[4‴-chloroanilinyl]-4-desoxypodophyllotoxin (Example 38); 4′-Demethyl-4β-anilinyl-4-desoxypodophyllotoxin (Example 19); 4′-Demethyl-4β-[4″-cyanoanilinyl]-4-desoxypodophyllotoxin (Example 20); 4′-Demethyl-4β-[3″-cyanoanilinyl]-4-desoxypodophyllotoxin (Example 21); 4′-Demethyl-4β-[4″-ethoxycarbonylanilinyl]-4-desoxypodophyllotoxin (Example 22); 4′-Demethyl-4β-[4″-morpholinoanilinyl]-4-desoxypodophyllotoxin (Example 23); 4′-Demethyl-4β-[3″,4″-methylenedioxyanilinyl]-4-desoxypodophyllotoxin (Example 24); 4′-Demethyl-4β-[3″,4″-dimethoxyanilinyl]-4-desoxypodophyllotoxin (Example 25); 4′-Demethyl-4β-[3″-pyridylamino]-4-desoxypodophyllotoxin (Example 30); 4′-Demethyl-4β-[2″-pyridylamino]-4-desoxypodophyllotoxin (Example 31); and 4′-Demethyl-4β-[3″-quinolinylamino]-4-desoxypodophyllotoxin (Example 32) equals or exceeds that of etoposide. In addition, as shown in Tables I and III, the DNA strand breakage abilities of 4′-Demethyl-4β-[2″-hydroxyethylamino]-4-desoxypodophyllotoxin (Example 5), 4′-Demethyl-4β-[2″-methoxyethylamino]-4-desoxypodophyllotoxin (Example 8), 4′-Demethyl-4β-[2″-hydroxypropylamino]-4-desoxypodophyllotoxin (Example 10), and 4′-Demethyl-4β-[1″-methyl-2″-hydroxyethylamino]-4-desoxypodophyllotoxin (Example 11), 4′-Demethyl-4β-[2″-aminoethoxy]-4-desoxypodophyllotoxin (Example 13); 4′-Demethyl-4β-[3-hydroxyanilinyl]-4-desoxypodophyllotoxin (Example 33), 4′-Demethyl-4β-[2-hydroxyanilinyl]-4-desoxypodophyllotoxin (Example 34), 4′-Demethyl-4β-[4-hydroxyanilinyl]-4-desoxypodophyllotoxin (Example 35), 4′-Demethyl-4β-[3″-fluoroanilinyl]-4-desoxypodophyllotoxin (Example 26); 4′-Demethyl-4β-[2″-fluoroanilinyl]-4-desoxypodophyllotoxin (Example 27); 4′-Demethyl-4β-[4″-fluoroanilinyl]-4-desoxypodophyllotoxin (Example 28); 4′-Demethyl-4β-[3″,5″-difluoroanilinyl]-4-desoxypodophyllotoxin (Example 29); 4′-Demethyl-4β-anilinyl-4-desoxypodophyllotoxin (Example 19); 4′-Demethyl-4β-[4″-cyanoanilinyl]-4-desoxypodophyllotoxin (Example 20); 4′-Demethyl-4β-[3″-cyanoanilinyl]-4-desoxypodophyllotoxin (Example 21); 4′-Demethyl-4β-[4″-ethoxycarbonylanilinyl]-4-desoxypodophyllotoxin (Example 22); 4′-Demethyl-4β-[4″-morpholinoanilinyl]-4-desoxypodophyllotoxin (Example 23); 4′-Demethyl-4β-[3″,4″-methylenedioxyanilinyl]-4-desoxypodophyllotoxin (Example 24); 4′-Demethyl-4β-[3″,4″-dimethoxyanilinyl]-4-desoxypodophyllotoxin (Example 25); 4′-Demethyl-4β-[3″-pyridylamino]-4-desoxypodophyllotoxin (Example 30); 4′-Demethyl-4β-[3″-quinolinylamino]-4-desoxypodophyllotoxin (Example 32); and 4′-Demethyl-4β-[4″-bromoanilinyl]-4-desoxypodophyllotoxin (Example 40) greatly exceeds that of etoposide.

Table II compares the relative DNA topoisomerase II inhibitory activity of several compounds of the present invention with etoposide. As shown in Table II, the compounds tested exhibited inhibitory activity exceeding that of etoposide by two to eight times.

Preparation of compounds within the scope of the present invention appear in the following examples.

EXAMPLE 1

Preparation of 4′-Demethylepipodophyllotoxin 5 g. (12.1 mmol) of podophyllotoxin were dissolved in 75 ml of anhydrous $CH_2Cl_2$. Dry hydrogen bromide gas was then bubbled through the solution to saturation. The reaction mixture was then capped and allowed to stand at room temperature for 48 hours. Removal of the solvent yielded a residue which was then treated with 25 ml of water, 50 ml of acetone and 5 g. of BaCO$_3$, and refluxed for one hour. The reaction mixture was extracted with chloroform and chromatographed on a silica gel column. The product was obtained by elution with chloroform-methanol (30:1) and recrystallized from CH$_2$Cl$_2$/ethylether to give 2.5 g. (52%) of 4'-Demethylepipodophyllotoxin. Spectral data agreed with that described by Kuhn, M., Keller-Julsen, C., and von Wartburg, A., *Helv. Chim. Acta,* 52, 944 (1969), which is herein specifically incorporated by reference. (See Scheme 1)

EXAMPLE 2

Preparation of 4'-Demethylpodophyllotoxin

4'-Demethylpodophyllotoxin was obtained using the silica gel column of Example 1 by further elution with chloroform-methanol (30:1). The product obtained by elution was crystallized from acetone in 5% (0.5 g) yield. Spectral data agreed with that described by Kuhn, M., and von Wartburg, A., *Helv. Chim. Acta,* 52, 948 (1969) (hereinafter Kuhn and von Wartburg), which is herein specifically incorporated by reference.

EXAMPLE 3

Preparation of 4'-Demethyl-4β-amino-4-desoxypodophyllotoxin. (Scheme II)

A. Preparation of 4'-0-Carbobenzoxyepipodophyllotoxin.

A solution of 2 g. of 4'-Demethylepipodophyllotoxin (5 mmol) in 200 ml of anhydrous dichloromethane was cooled in an ice bath, and treated with 2.5 ml of triethylamine (18 mmol), and 2.5 ml of carbobenzoxychloride (17.5 mmol). The reaction mixture was stirred at room temperature for 2 hours after which time 100 ml of water was added. The organic layer was dried using MgSO$_4$, concentrated, and purified using silica gel column chromatography. The product was obtained upon elution with chloroform and recrystallized from chloroform/ethanol to give 2.4 g. (89%). Spectral data agreed with that described by Kuhn and von Wartburg.

B. Preparation of 4'-0-Carbobenzoxy-4-epiazidopodophyllotoxin.

A solution of 3 g. (5.6 mmol) of 4'-0-Carbobenzoxy-4-epipodophyllotoxin (the product of Example 3) in 100 ml of anhydrous methylene chloride was cooled in an ice bath and treated successively with 1.5 ml (10.8 mmol) of triethylamine, and 1.2 ml (15.5 mmol) of methanesulfonylchloride. The ice bath was then removed and the reaction mixture was stirred at room temperature for one hour. This mixture was then evaporated in vacuo to dryness, and 40 ml of anhydrous DMF was added along with 3 g. (46 mmol) of sodium azide. The reaction mixture was stirred overnight at room temperature and then partitioned between water (100 ml) and ethylacetate. The organic layer was washed with water, dried using MgSO$_4$, and concentrated to yield a crude residue, which was checked by TLC and NMR analyses to be a mixture of 4α- and 4β-azido isomers (ca.1:3). Crystallization from chloroform/ethanol provided the pure β-isomer 4'-O-Carbobenzoxy-4-epiazidopodophyllotoxin (2.3 g, 73%) having the following properties: mp.202°-204° C.; MS, m/z 559 (M+), 424, and 382; IR KBr) 2950, 2900, 2100 (azide), 1770 (carbonate C=O), 1745 (lactone C=O), 1600, and 1475 (aromatic C=C) cm$^{-1}$; $^1$H NMR (CDCl$_3$) δ7.40 (m, 5H, cbz aromatic), 6.82 (s, 1H, 5-H), 6.58 (s, 1H, 8-H), 6.27 (s, 2H, 2'.6'-H), 6.03 (ABq, J=2.4 Hz, 2H, O—CH$_2$—O), 5.25 (s, 2H, OCH$_2$Ph), 4.77 (d, J=4 Hz, 1H, 4-H), 4.65 (d, J=5 Hz, 1H, 1-H), 4.31 (d, J=9 Hz, 2H, 11, 11'-H), 3.66 (s, 6H, 3',5'-OCH$_3$), 3.2(dd, J=5,14 Hz, 1H, 2-H), and 2.90 (m,1H, 3-H); Anal. (C$_{29}$H$_{25}$O$_9$N$_3$½H$_2$O), C.H.

C. Preparation of 4'-Demethyl-4β-amino-4-desoxypodophyllotoxin.

500 mg of 10% palladium on carbon was added to a solution of the crude 4'-demethyl-4-azidopodophyllotoxin (2.3g, 4.1 mmol), obtained according to steps A and B, and 200 ml of ethylacetate. This mixture was shaken under 40 psi of hydrogen for four hours. The reaction mixture was then filtered over celite and the filtrate evaporated in vacuo. The residue was chromatographed on a silica gel column and eluted first with a chloroform/ethylacetate (2:1) solvent system to remove the non-polar products. Further elution with a chloroform/methanol (19:1) mobile phase yielded 0.85 g, (52%) of the desired product. The product was then crystallized from methylene chloride/ethylether and had the following properties: mp 132°-135° C.; MS m/z 399 (M+); IR (KBr) 3360 (OH), 3290 (primary amine), 2900 (aliphatic C-H), 1745 (lactone), 1590 (aromatic C-H) cm$^{-1}$; $^1$H NMR (CDCl$_3$) δ6.81 (s, 1H,5-H), 6.49 (s, 1H, 8-H), 6.30 (s, 2H, 2',6'-H), 5.96 (ABq, J=1 Hz, 2H, OCH$_2$O), 5.3 (s, 1H, OH, D$_2$O exchangeable), 4.55 (d, J=5.2 Hz, 1H, 1-H), 4.28 (d, J=9.5 Hz, 2H, 11,11'-H), 4.17 (d, J=4.1 Hz, 1H, 4-H) 3.77 (s, 6H, 3',5'-OCH$_3$), 3.28 (dd, J=5.2,14 Hz, 1H, 2-H), and 2.85 (m, 1H, 3-H); Anal. (C$_{21}$H$_{21}$O$_7$NH$_2$O), C.H.

EXAMPLE 4

Preparation of 4'-Demethyl-4α-amino-4-desoxypodophyllotoxin

4'-Demethyl-4α-amino-4-desoxypodophyllotoxin was obtained from the column used in Example 3 by further elution with a chloroform/methanol (19:1) mobile phase. The pure product (0.34 g, 20%) was crystallized from methylene chloride/ethylether and had the following properties: mp 133°-135° C.; MS m/z 399 (M+); IR (KBr) 3360 (OH), 3295 (NH$_2$), 2900 (aliphatic C-H), 1743 (lactone), 1590 (aromatic C-H) cm$^{-1}$; $^1$H NMR (CDCl$_3$) δ7.14 (s, 1H, 5-H), 6.54 (s, 1H, 8-H), 6.20 (s, 2H, 2',6'-H), 6.00 (ABq, J=1 Hz, 2H, OCH$_2$O), 4.63 (d, J=5.1 Hz, 1H, 1-H), 4.61 (d, J=9.0 Hz, 1H, 11α-H), 4.07 (dd, J=9.0,10.4 Hz, 1H, 11β-H), 3.83 (d, J=10.3 Hz, 1H, 4-H), 3.81 (s, 6H, 3',5'-OCH$_3$), 2.85 (dd, J=5.1,14.1 Hz, 1H, 2-H), and 2.57(m, 1H, 3-H); Anal. (C$_{21}$H$_{21}$O$_7$N.H$_2$O), C.H.

EXAMPLES 5-12

Preparation of 4-alkylamino-4-desoxypodophyllotoxins. (Scheme III)

The 4-alkylamino-4-desoxypodophyllotoxins specified in Examples 5-12 were prepared according to the following procedure. A solution of podophyllotoxin (5 g, 12.1 mmol) in 50 ml of anhydrous methylenechloride was kept at room temperature and dry hydrogen bromide gas was bubbled through the solution until saturation was achieved. The flask was then capped and allowed to stand for 48 hours after which time dry nitrogen was bubbled through the solution to drive off excess HBr. Then 2 g. of anhydrous BaCO$_3$ and 2 ml of the appropriate amine were added. Vigorous evolution of gas was observed. The mixture was allowed to stand for 5 hours at room temperature after which the reaction mixture was filtered, washed with water, dried, and purified via column chromatography. Yields ranged from 5-10%. The products obtained in these examples had the characteristics listed below.

EXAMPLE 5

4'-Demethyl-4β-[2''-hydroxyethylamino]-4-desoxypodophyllotoxin

Amorphous powder from CH$_2$Cl$_2$-ether: mp 120° C.; MS m/z 443 (M+); IR (KBr) 3420 (NH,OH), 2900 (aliphatic C-H), 1755 (lactone), 1600, and 1475 (aromatic C=C) cm$^{-1}$; $^1$H NMR (CDCl$_3$) δ6.82 (s, 1H, 5-H), 6.49 (s, 1H, 8-H), 6.29 (s, 2H, 2',6'-H), 5.97 (ABq, J=1.0,4.4 Hz, 2H, OCH$_2$O), 4.57 (d, J=5.0 Hz, 1H, 1-H), 4.35 (m, 2H, 11,11'-H), 3.93 (d, J=4.0 Hz, 1H, 4-H), 3.79 (s, 6H, 3',5'-OCH$_3$), 3.76 (m, 2H, 2''-H), 3.3 (dd, J=5.0,13.5 Hz, 1H, 2-H), 3.09 (m. 1H, 3-H), and 2.75 (m, 2H, 1''-H); Anal. (C$_{23}$H$_{25}$O$_8$N.½H$_2$O), C.H.

EXAMPLE 6

4'-Demethyl-4α-[2''-hydroxyethylamino]-4-desoxypodophyllotoxin

Crystals from CH$_2$Cl$_2$-ether: mp 230°-234° C.; MS m/z 443 (M+); IR (KBr) 3425 (NH,OH), 2900 (aliphatic C-H), 1753 (lactone), 1600, and 1475 (aromatic C=C) cm$^{-1}$;$^1$H NMR (CD$_3$OD) δ6.83 (s, 1H, 5-H), 6.47 (s, 1H, 8-H), 6.38 (s, 2H, 2',6'-H), 5.92 (ABq, J=1.0,14.3 Hz, 2H, OCH$_2$O), 4.40 (s, 1H, 11-H), 4.25 (s, 1H, 11'-H), 3.75 (s, 6H, 3',5'- OCH$_3$), 3.65 (m, 4H, 1'',2''-H), 3.56 (m, 1H, 1-H), 3.49 (dd, J=6.1,11.3 Hz, 1H, 4-H), 2.87 (ddd, J-5.1, 6.3, 13.5, 1H, 3-H), and 2.67 (dd, J=6.1, 8.2, 1H, 2-H); Anal. (C$_{23}$H$_{25}$O$_8$N.½H$_2$O), C.H.

EXAMPLE 7

4'-Demethyl-4β-propylamino-4-desoxypodophyllotoxin

Crystals from CH$_2$Cl$_2$-ether: mp 153°-156° C.; MS m/z 441 (M+); IR (KBr) 3470 (OH), 3320 (NH), 1750 (lactone), 1600, and 1475 (aromatic C=C) cm$^{-1}$; $^1$H NMR (CDCl$_3$) δ6.77 (s, 1H, 5-H), 6.47 (s, 1H, 8-H), 6.28 (s, 2H, 2',6'-H), 5.95 (ABq, J=1.2,5.0 Hz, 2H, OCH$_2$O), 4.30 (d, J=5.0 Hz, 1H, 1-H), 4.30 (d, J=4.0 Hz, 1H, 4-H), 4.28(m, 2H, 11,11'-H), 3.78(s, 6H, 3',5'-OCH$_3$), 3.30 (dd, J=5.0, 13.9 Hz, 1H, 2-H), 2.83 (m, 2H, 1''-H), 2.52 (m, 1H, 3-H), 1.55(m, 2H, 2''-H), and 0.95 (t, J=7.6 Hz, 3H, 3''-H); Anal. (C$_{24}$H$_{27}$O$_7$N ½H$_2$O), C.H.

EXAMPLE 8

4'-Demethyl-4β-[2''-methoxyethylamino]-4-desoxypodophyllotoxin

Crystals from CH$_2$Cl$_2$-ether: mp 202°-204° C.; MS m/z 457 (M+); IR (KBr) 3440 (OH, NH), 1750 (lactone), 1600, and 1475 (aromatic C=C) cm$^{-1}$; $^1$H NMR (CDCl$_3$) δ6.80 (s, 1H, 5-H), 6.44 (s, 1H, 8-H), 6.25 (s, 2H, 2',6'-H), 5.92 (ABq, J=1.0,5.0 Hz, 2H, OCH$_2$O), 4.50 (d, J=5.4 Hz, 1H, 1-H), 4.28 (m, 2H, 11,11'-H), 3.88 (d, J=4.0 Hz, 1H, 4-H), 3.75 (s, 6H, 3',5'-OCH$_3$), 3.52 (m, 2H, 2''-H), 3.37 (s, 3H, 3''-H), 3.38 (dd, J=14.4,5.4 Hz, 1H, 2-H), 3.05 (m, 1h, 3-H), and 2.75 (m, 2H, 1''-H); Anal. (C$_{24}$H$_{27}$O$_8$N.½H$_2$O), C.H.

EXAMPLE 9

4'-Demethyl-4β-allylamino-4-desoxypodophyllotoxin

Amorphous powder from CH$_2$Cl$_2$-ether: mp 225°-228° C.; MS m/z 439 (M+); IR (KBr) 3340 (OH, NH), 2885 (aliphatic C-H), 1745 (lactone), 1600, and 1475 (aromatic C=C) cm$^{-1}$; $^1$H NMR (CDCl$_3$) δ 6.77 (s, 1h, 5-H), 6.49 (s, 1H, 8-H), 6.28 (s, 2H, 2',6'-H), 5.95 (ABq, J=1.0, 4.5 Hz, 2H, OCH$_2$O), 5.90 (m, 1H, 2''-H), 5.4 (m, 1H, N-H, D$_2$O exchangeable), 5.22 (dd, J=4.0, 17.5 Hz, 2H, 3''-H), 4.53 (d, J=5.5 Hz, 1H, 1-H), 4.30 (m, 2H, 11,11'-H), 3.88 (d, J=3.6 Hz, 1H, 4-H), 3.75 (s, 6H, 3',5'-OCH$_3$), 3.30 (dd, J=5.4, 14.4 Hz, 1H, 2-H), 3.30 (m, 1H, 1''-H), and 2.80 (m, 1H, 3-H); Anal. (C$_{24}$H$_{25}$O$_7$N.2.2 H$_2$O), C.H.

EXAMPLE 10

4'-Demethyl-4β-[2''-hydroxypropylamino]-4-desoxypodophyllotoxin

Crystals from CH$_2$Cl$_2$-ether: mp 145-°150° C.; MS m/z 457 (M+); IR (KBr) 3330 (OH, NH), 2890 (aliphatic C-H), 1750 (lactone), 1600, and 1475 (aromatic C=C) cm$^{-1}$; $^1$H NMR (CDCl$_3$) δ6.83 (s, 1h, 5-H), 6.47 (s, 1H, 8-H), 6.27 (s, 2H, 2',6'-H), 5.95 (ABq, J=1.0, 6.3 Hz, 2H, OCH$_2$O), 5.40 (m, 1h, N-H, D$_2$O exchangeable ), 4.54 (d, J=4.6 Hz, 1H, 1-H), 4.30 (m, 2H, 11,11'-H), 3.85 (m, 1H, 2''-H), 3.85 (d, J=3.8 Hz, 1H, 4-H), 3.75 (s, 6H, 3',5'-OCH$_3$), 3.25 (dd, J=4.6, 13.8 Hz, 1H, 2-H), 2.85 (dd, J=6.8, 12.5 Hz, 1H, 1''-H), 2.82 (m, 1h, 3-H), 2.63 (dd, J=3.8, 12.5 Hz, 1H, 1''-H), and 1.20 (d, J=6.3 Hz, 3H, 3''-H); Anal. (C$_{24}$H$_{25}$O$_8$N.½H$_2$O), C.H.

EXAMPLE 11

4'-Demethyl-4β-[1'''-methyl-2''-hydroxyethylamino]-4-desoxypodophyllotoxin

Amorphous powder from CH$_2$Cl$_2$-ether: mp 220°-225° C.; MS m/z 457 (M+);$^1$H NMR (CDCl$_3$) δ6.89 (s, 1H, 5-H), 6.47 (s, 1H, 8-H), 6.27 (s, 2H, 2',6'-H), 5.95 (ABq, J=1.0, 4.5 Hz, 2H, OCH$_2$O), 5.40 (m, 1H, N-H, D$_2$O exchangeable), 4.52 (d, J=4.8 Hz, 1H, 1-H), 4.30 (d, J=9.0 Hz, 2H, 11,11'-H), 4.00 (d, J=4.0 Hz, 1H, 4-H), 3.74 (s, 6H, 3',5'-OCH$_3$), 3.50 (m, 2H, 2''-H), 3.22 (dd, J=4.8, 13.5 Hz, 1H, 2-H), 2.85 (m, 1H, 3-H), 2.82 (m, 1H, 1''-H)m and 1.05 (d, J=6.3 Hz, 3H, 1'-CH$_3$); Anal. (C$_{24}$H$_{25}$O$_8$N.½H$_2$O), C.H.

EXAMPLE 12

4'-Demethyl-4β-[3''-hydroxypropylamino]-4-desoxypodophyllotoxin

Crystals from CH$_2$Cl$_2$-ether: mp 193-°196° C.; MS m/z 457 (M+); IR (KBr) 3460 (OH) 3320 (NH), 2900 (aliphatic C-H), 1740 (lactone), 1600, and 1475 (aromatic C=C) cm$^{-1}$; $^1$H NMR (CDCl$_3$) δ6.75 (s, 1H, 5-H), 6.46 (s, 1H, 8-H), 6.24 (s, 2H, 2',6'-H), 5.94 (ABq, J=1.0,4.4 Hz, 2H, OCH$_2$O), 4.52 (d, J=5.3 Hz, 1H, 1-H), 4.33 (dd, J=7.9,8.0 Hz, 1H, 11-H), 4.23 (dd, J=8.0,10.7 Hz, 11'-H), 3.78 (d, J=4.0 Hz, 1H, 4-H), 3.73 (s, 6H, 3',5'-OCH$_3$), 3.72 (t, 2H, 3''-H), 3.21 (dd, J=5.3,14.0 Hz, 1H, 2-H), 3.11 (dd, J=5.9,11.4 Hz, 1H, 1''-H), 2.64 (ddd, J=14.0,7.0,11.0 Hz, 1H, 1''-H) and 1.75 (m, 2H, 2''-H); Anal. (C$_{24}$H$_{27}$O$_8$N.½H$_2$O), C.H.

EXAMPLE 13

Preparation of 4'-Demethyl-4β(2''-aminoethoxy)-4-desoxypodophyllotoxin. (Scheme IV)

4'-Demethyl-4β(2''-aminoethoxy)-4-desoxypodophyllotoxin was prepared according to the following procedure.

A. 4'-Demethyl-4β-(2''-bromoethoxy)-4-desoxypodophyllotoxin.

Podophyllotoxin (500 mg) was suspended in anhydrous dichloromethane (15 ml). Dry hydrogen bromide gas was bubbled through the mixture until saturation was achieved. The flask was then capped and allowed to stand at room temperature for 48 h. After bubbling nitrogen gas through the solution to drive off excess hydrogen bromide gas, barium carbonate (1.50 g) and 2-bromoethanol (1 ml) were added and stirred at room temperature for 10 h. The mixture was diluted with dichloromethane, filtered and evaporated to dryness. The syrupy residue was purified by silica gel column chromatography eluting with chloroform-acetone (30:1 v/v). For further purification the product was chromatographed on silica gel column using toluene-ethylacetate (5:1 v/v) as an eluant. Yield (218 mg). mp 194°–195° C. $^1$H-NMR (CDCl$_3$): δ6.79 (1H, S, 5-H), 6.56 (1H, S, 8-H), 6.25 (2H, S, 2', 6'-H), 6.00–5.97 (each d, J=1.2 Hz, OCH$_2$O), 5.40 (H, S, 4-OH), 4.88 (1H, dd, J=7.60, 8.34 Hz, 11-H), 4.61 (1H, d, J=5.2 Hz, 1-H), 4.50 (2H, m), 4.04 (1H, m), 3.80 (1H, m), 3.77 (6H, S, 2×OCH$_3$), 3.47 (2H, m), 3.42 (1H, dd, J=5.39, 14.08 Hz, 2-H), 2.90 (1H, m, 3-H)

Anal. Calcd. for C$_{23}$H$_{23}$BrO$_8$: C, 54.45; H, 4.57. Found: C, 54.35; H, 4.60.

B. 4'-Demethyl-4β-(2''-azidoethoxy)-4-desoxypodophyllotoxin.

The mixture of 4'-demethyl-4β-(2-bromoethyl) epipodophyllotoxin (157 mg) and sodium azide (150 mg) in N,N-dimethylformamide (6 ml) was stirred for 10 h at room temperature. Pouring the reaction mixture into water and stirring gave a white precipitate, which was collected by filtration and dried in the air. Recrystallization from chloroform-ether gave pure product (120 mg). mp 215°–217° C. IR (CHCl$_3$) cm$^{-1}$: 3538 (OH), 2205 (N$_3$), 1770 (lactone), 1615 (aromatic C=C) Anal. Calcd. for C$_{23}$H$_{23}$N$_3$O$_8$: C, 58.84; H, 4.93; N, 8.95. Found: C, 58.78; H, 4.98; N, 9.28.

C. 4'-Demethyl-4β(2''-aminoethoxy)-4-desoxypodoplyllotoxin.

A mixture of 4'-Demethyl-4β-(2'''-azidoethyl-)epipodophyllotoxin (108 mg) and 10% palladium in carbon (55 mg) in ethylacetate (20 ml) was stirred under a hydrogen atmosphere for 5 h. After the removal of the catalyst by filtration, the filtrate was evaporated to dryness under reduced pressure. The crude product was purified by silica column chromatography eluting with chloroform-methanol (5:1 v/v) to obtain pure material (82 mg) having the following characteristics. mp 143°–145° C.

Anal. Cald. for C$_{23}$H$_{25}$NO$_8$H$_2$O: C, 58.72; H, 6.00; N, 2.97. Found: C, 58.74; H, 5.98; N, 2.97.

EXAMPLE 14

Preparation of 4'-Demethyl-4β-(2''-hydroxyethoxy)-4-desoxypodophyllotoxin. (Scheme V)

Podophyllotoxin (200 mg) was suspended in anhydrous dichloromethane (15 ml). Dry hydrogen bromide gas was bubbled through the mixture until saturation was achieved. The flask was then capped and allowed to stand at room temperature for 48 h. After bubbling nitrogen gas through the solution to drive off excess hydrogen bromide gas, anhydrous barium carbonate (500 mg) and ethyleneglycol (500 mg) were added and stirred at room temperature for 10 h. The mixture was diluted with dichloromethane, filtered, washed with water and the organic layer was dried over anhydrous MgSO$_4$. The removal of solvent gave a syrup, which was purified by silica gel column chromatography eluting with chloroform-acetone (30:1 v/v) to obtain pure product (80 mg). The resulting product had the following properties:

$^1$H-NMR (CDCl$_3$): δ6.82 (1H, S, 5-H), 6.51 (1H, S, 8-H), 6.23 (2H, S, 2', 6'-H), 5.95 (2H, S,OCH$_2$O), 5.52 (1H, S, OH), 4.70 41.5 (m), 3.72 (s, 6H, 3',5'-OCH$_3$).

EXAMPLE 15

Preparation of 4'-demethyl-4β-Chloro-4-desoxypodophyllotoxin. (Scheme VI)

Methylsulfide (0.3 ml) and N-chlorosuccinimide (60 mg, 0.45 mmole) were added at 0° C. to a solution of 4'-demethylpodophyllotoxin (100 mg, 0.25 mmole) in methylene chloride (15 ml). The mixture was stirred for 5 h at 0° C. under a nitrogen atmosphere. After the removal of the volatile reagents by evaporation in vacuo, the residue was purified by silica gel chromatography eluting with methylene chloride and acetone to obtain the pure product (82 mg, 78.5%). The product had the following properties:

IR(CHCl$_3$) cm$^{-1}$: 3540(OH), 1770(lactone)

$^1$H-NMR(CDCl$_3$) δ:6.57 (s, 1H, 8-H), 6.53 (s, 1H, 5-H), 6.30 (s, 2H, 2'6'-H), 6.02, 5.98 (each d, 2H, J=1.3 Hz, OCH$_2$O), 5.42 (s, 1H, OH), 4.62 (d, 1H, J=5.2 Hz, 1-H), 4.53 (m, 2H, 11-CH$_2$), 4.45 (d, 1H, J-3.3 Hz, 4-H), 3.80 (s, 6H, 3', 5'-OCH$_3$), 3.41 (dd, 1H, J-5.3, 14 Hz, 2-H), 2.86 (m, 1H, 3-H)

EXAMPLES 16, 17, AND 18

Preparation of 4, 5, 8, 2'-tetrabromo-4 β-desocypodophyllotoxin, 5, 2', 6'-tribromo-4β-desoxypodophyllotoxin, and 5, 8, 2',6'-tetrabromo-4β-desoxypodophyllotoxin.(Scheme VII)

The compounds of Examples 16,17, and 18 were prepared according to the following procedure. To a solution of podophyllotoxin (200 mg, 0.54 mMol) in CHCl$_3$ (7 ml) was added bromine (0.5 ml, 9.70 mMol). After stirring for 2 h. at room temperature, the mixture was poured into ice-water, and extracted with CHCl$_3$, followed by washing with 5% sodium hydrosulfite to remove excess bromine. The organic layer was dried over anhydrous magnesium sulfate, filtered, and concentrated in vacuo to yield a crude product. This was purified by use of preparative TLC (CHCl$_3$-acetone 15:1) to obtain the compounds of Example 16, 17, and 18.

EXAMPLE 16

4, 5, 8, 2'-tetrabromo-4β-desoxypodophyllotoxin: 16 mg; NMR (CDCl$_3$) δ6.21 (d, J=1.0 Hz, 2H, OCH$_2$O), 5.85 (s, 1H, 6'-H), 5.74 (d, J=3.2 Hz, 1H, 4-H), 5.45 (d, J=6.4 Hz, 1H, 1-H), 4.49 (m, 2H, 11,11'-H), 3.95 (s, 3H, 3'-OCH$_2$), 3.92 (s, 3H, 4'-OCH$_3$), 3.68 (s, 3H, 5'-OCH$_3$), 3.44 (dd, J=6.4, 14.4 Hz, 1H, 2-H) and 3.35 (m, 1H, 3-H); IR (CHCl$_3$) no OH band, 1785 (lactone) cm$^{-1}$.

EXAMPLE 17

5, 2', 6'-tribromo-4β-desoxypodophyllotoxin: 60 mg: NMR (CDCl$_3$) δ6.33 (s, 1H, 8-H), 6.04 (d, J=1.0 Hz, 2H, OCH$_2$O), 5.72 (d, J=9.5 Hz, 1H, 1-H), 5.25 (br.s, 1H, 4-H), 4.40 (m, 2H, 11, 11'-H), 4.95 (s, 3H, 3'-OCH$_3$), 3.94 (s, 3H, 5'-OCH$_3$), 3.81 (s, 3H, 4'-OCH$_3$), 3.70 (m, 1H, 3-H), and 3.55 (dd, J=9.5, 15.0 Hz, 1H, 2-H: IR (CHCl₃) 3600 (OH), 1776 (lactone) CM⁻¹.

EXAMPLE 18

5, 8, 2', 6'-tetrabromo-4β-desoxydophyllotoxin: 16 mg; NMR (CDCl₃) δ6.14 (d, J=2.2, 2H, OCH₂O), 5.70 (d, J=7.6, 1H, 1-H), 5.21 (d, J=2.8 Hz, 1H, 4-H), 4.40 (m, 2H, 11,11'-H 3.93 (s, 6H, 3' and 5'-OCH₃), 3.78 (s, 3H, 4'-OCH₃), 3.65 (m, 1H, 3-H) and 3.49 (dd, J=9.5, 15 Hz, 1H, 2-H); IR (CHCl₃) 3600 (OH), 1776 (lactone) cm⁻¹.

16, R₁=R₂=R₃=R₅=Br, R₄=H
17, R₁=OH, R₂=R₄=R₅=Br, R₃=H
18, R₁=OH, R₂=R₃=R₄=R₅=Br

EXAMPLE 19-41

Preparation of 4'demethyl-4β-(arylamino)-4-desoxypodophyllotoxins (19-41). (Scheme VIII)

The 4'-demethyl-4β-(arylamino)-4-deoxypodophyllotoxins specified in examples 19-41 were prepared according to the following procedure:

A solution of 4'-demethylepipodophyllotoxin (10 g, 24 mmol) in 250 ml of dry dichloromethane was kept at 0° C., and dry hydrogen bromide gas was bubbled through the solution. After 30 min., nitrogen was bubbled through the solution to drive off excess hydrogen bromide. The solution was then evaporated in vacuum to dryness by means of azeotropic distillation with benzene.

The desired product (11.5 g) was obtained and then used for the next step reaction without any further purification.

Spectral data agreed with that described by M. Kuhn and A. Von Wartburg. Helv. Chim. Acta, 52, 944 (1969).

A solution containing 4'-demethyl-4β-bromo-4-deoxypodophyllotoxin (300 mg, 0.65 mmol), barium carbonate (153 mg, 0.78 mmol) and the appropriate arylamines (0.78 mmol) in 7 ml of dry 1,2-dichloroethane was stirred overnight at room temperature. The reaction mixture was filtered, diluted with ethyl acetate, washed with water, dried and purified via column chromatography. The products (19-41) obtained in the examples had the characteristics listed below.

EXAMPLE 19

4'-Demethyl-4β-anilinyl-4-desoxypodophyllotoxin

Crystals from methanol; mp 172°-173°, $[\alpha]^{25}_D$-120° (C=1.0, CHCl₃); IR (KBr) 3500 (OH), 3360 (NH), 2900 (aliphatic C-H), 1755 (lactone), 1595, 1500 and 1475 (aromatic c=c) cm⁻¹:¹H NMR CDCl₃ δ7.22 (t, J=7.5 Hz, 2H, 3", 5"-H), 6.80 (m, 2H, 4"-H and 5-H), 6.50 (m, 3H, 2"-H, 6"-H and 8-H), 6.33 (s, 2H, 2', 6'-H), 5.97 (AB$_q$, J=1.3, 3.6 Hz, OCH₂O), 5.42 (s, 1H, exchangeable, 4'-OH), 4.68 (br, 1H, 4-H), 4.60 (d, J=4.9 Hz, 1-H), 4.38 (t, J=8.4 Hz, 1H, 11-H), 4.01 (t, J=8.4 Hz, 1H, 11-H), 3.85 (br, 1H, exchangeable, NH), 3.79 (s, 6H, 3', 5'-OCH₃), 3.16 (dd, J=5.0, 14.0 Hz, 1H, 2-H), 3.00 (m, 1H, 3-H).

Anal. (C₂₇H₂₅NO₇), C.H.N.

EXAMPLE 20

4'-Demethyl-4β-[4"-cyanoanilinyl]-4-desoxypodophyllotoxin

Crystals from ethanol; mp 187°-189°, $[\alpha]^{25}_D$-145° (C=1.0, CHCl₃); IR (KBr) 3500 (OH), 3360 (NH), 2890 (aliphatic C-H), 2210 (lactone), 1600, 1510 and 1475 (aromatic C=C) cm⁻¹: ¹H NMR CDCl₃ δ7.50 (d, J=8.7 Hz, 2H, 3", 5"-H), 6.74 (s, 1H, 5-H), 6.57 (d, J=8.7 Hz, 2H, 2", 6"-H), 6.55 (s, 1H, 8-H), 6.32 (s, 2H, 2', 6'-H), 5.99 (AB$_q$, J=1.2, 8.3 Hz, 2H, OCH₂O), 5.44 (s, 1H, exchangeable, 4'-OH), 4.78 (m, 1H, exchangeable, NH), 4.63 (d, J=4.2 Hz, 1H, 4-H), 4.36 (m, 2H, 11-H), 3.85 (m, 1H, 1-H), 3.79 (s, 6H, 3', 5'-OCH₃), 3.09 (dd, 1H, 2-H), 3.05 (m, 1H, 3-H).

Anal. (C₂₈H₂₄NO₇), C.H.N.

EXAMPLE 21

4'-Demethyl-4β-[3"-cyanoanilinyl]-4-desoxypodophyllotoxin

Crystals from methanol; mp 191°-192°, $[\alpha]^{25}_D$-117° (C=0.33, CHCl₃); IR (KBr) 3450 (OH), 3360 (NH), 2900 (aliphatic C-H), 2225 (CN), 1750 (lactone), 1595, 1500 and 1450 (aromatic C=C) cm⁻¹: ¹H NMR CDCl₃ δ7.31 (t, J=7.6 Hz, 5"-H), 7.07 (d, J=7.6 Hz, 4"-H), 6.80 (d, 2H, 2"-H and 6"-H), 6.74 (s, 1H, 5-H), 6.55 (s, 1H, 8-H), 6.33 (s, 2H, 2', 6'-H), 6.00 (d, J=7.0 Hz, 2H, OCH₂O), 5.48 (s, 1H exchangeable, 4'-OH), 4.69 (d, J=3.8 Hz, 1H, 4-H), 4.62 (d, J=4.5 Hz, 1H, 2-H), 4.41 (t, J=8.5 Hz, 1H, 11-H), 3.92 (t, J=8.5 Hz, 1H, 11-H), 3.81 (s, 6H, 3', 5'-OCH₃), 3.14-3.00 (m, 2H, 2-H and 3-H).

Anal. (C₂₈H₂₄N₂O₇)·½H₂O, C.H.N.

EXAMPLE 22

4'-Demethyl-4β-[4"-ethoxycarbonylanilinyl]-4-desoxypodophyllotoxin

Crystals from ethanol; mp 270°-271°, $[\alpha]^{25}_D$-145° (C=0.33, CHCl₃); IR (KBr) 3500 (OH), 3370 (NH), 2940 (aliphatic C-H), 1762 (lactone), 1695 (ester), 1610, 1520 and 1480 (aromatic C=C) cm⁻¹: ¹H NMR CDCl₃ δ7.92 (d, J=8.8 Hz, 2H, 3", 5"-H), 6.77 (s, 1H, 5-H), 6.55 (d, J=8.8 Hz, 2H, 2", 6"-H), 6.54 (s, 1H, 8-H), 6.33 (s, 2H, 2', 6'-H), 5.99 (AB$_q$, J=1.1, 8.2 Hz, 2H, OCH₂O), 5.44 (s, 1H, exchangeable, 4'-OH), 4.78 (d, J=3.3 Hz, 1H, 4-H), 4.62 (d, J=4.5 Hz, 1H, 1-H), 4.40 (m, 2H, 4-H and 11-H), 4.37 (q, J=7.1 Hz, 2H, CO₂CH₂CH₃), 4.32 (d, J=7.1, 1H, exchangeable, NH), 3.92 (t, J=7.5 Hz, 1H, 11-H), 3.80 (s, 6H, 3', 5'-OCH₃), 3.10 (dd, 1H, 2-H), 3.08 (m, 1H, 3-H), 1.38 (t, J=7.1 Hz, 3H, CO₂CH₂CH₃).

Anal. (C₃₀H₂₉NO₉), C.H.N.

EXAMPLE 23

4'-Demethyl-4β-[4"-morpholinoanilinyl]-4-desoxypodophyllotoxin

Crystals from ethanol; mp 235°-237°, $[\alpha]^{25}_D$-129° (C=1, CHCl₃); IR (KBr) 3500 (OH), 3300 (NH), 2880 (aliphatic C-H), 1755 (lactone), 1620, 1510 and 1475 (aromatic C=C) cm⁻¹: ¹H NMR CDCl₃ δ6.86 (d, J=9.5 Hz, 2H, 3", 5"-H), 6.76 (s, 1H, 5-H), 6.52 (br, 3H, 8-H and 2", 6"-H), 6.35 (s, 2H, 2', 6'-H), 5.96 (d, J=66.7 Hz, 2H, OCH₂O), 5.44 (s, 1H, exchangeable, 4'-OH), 4.61 (m, 2H, 4-H and 1-H), 4.37 (t, J=7.0 Hz, 1H, 11-H), 4.08 (t, J=7.0 Hz, 1H, 11-H), 3.82 (br, 4H), 3.80 (s, 6H, 3', 5'-OCH₃), 3.22-2.90 (m, 2H, 2-H, 3-H and 4H,

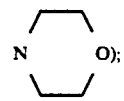

Anal. ($C_{31}H_{32}N_2O_8$), C.H.N.

EXAMPLE 24

4'-Demethyl-4β-[3″,4‴-(methylenedioxy)anilinyl]-4-desoxypodophyllotoxin

Crystals from methanol; mp 247°-2497°, $[α]^{25}_D$-126° (C=1, $CHCl_3$); IR (KBr) 3500 (OH), 3340 (NH), 2900 (aliphatic C-H), 1752 (lactone), 1605, 1496 and 1475 (aromatic C=C) $cm^{-1}$; $^1H$ NMR $CDCl_3$, δ6.76 (s, 1H, 5-H), 6.68 (d, J=8.1 Hz, 1H, 5″-H), 6.52 (s, 1H, 8-H), 6.33 (s, 2H, 2′, 6′-H), 6.17 (d, J=1.2 Hz, 1H, 2″-H), 5.96 (q, J=1.2, 8.1 Hz, 3H, 6″H and $OCH_2O$), 5.90 (s, 2H, 7″-H), 5.43 (s, 1H exchangeable, 4'-OH), 4.59 (d, J=4.9 Hz, 1H, 4-H), 4.56 (d, J=3.9 Hz, 1H, 1-H), 4.37 (t, 1H, 11-H), 4.05 (t, 1H, 11-H), 3.79 (s, 6H, 3′, 5′-$OCH_3$), 3.15 (dd, 1H, 2-H), 2.95 (m, 1H, 3-H).

Anal. ($C_{28}H_{25}NO_9$), C.H.N.

EXAMPLE 25

4'-Demethyl-4β-[3″,4″-dimethoxyanilinyl]-4-desoxypodophyllotoxin

Crystals from methanol; mp 233°-234° (dec); $[α]^{25}_D$-118° (C=1, $CHCl_3$); IR (KBr) 3500 (OH), 3360 (NH), 2920 (aliphatic C-H), 1770 (lactone), 1605, and 1505 (aromatic C=C) $cm^{-1}$; $^1H$ NMR $CDCl_3$, δ6.78 (s, 1H, 5-H), 6.75 (d, J=8.5 Hz, 1H, 5″-H), 6.53 (s, 1H, 8-H), 6.34 (s, 2H, 2′, 6′-H), 6.17 (s, 1H, 2″-H), 6.05 (d, J=8.5 Hz, 1H, 6″-H), 5.96 (d, J=2.4 Hz, 2H, $OCH_2O$), 5.43 (s, exchangeable, 4'-OH), 4.60 (d, 2H, 4-H and 1-H), 4.38 (t, J=8.3 Hz, 1H, 11-H), 4.05 (t, J=8.3 Hz, 1, 11-H), 3.83 (s, 3H, 4″-$OCH_3$), 3.81 (s, 3H, 3″-$OCH_3$), 3.80 (s, 6H, 3′, 5′-$OCH_3$), 3.18 (dd, J=5.0, 14.0 Hz, 1H, 2-H), 2.96 (m, 1H, 3-H).

Anal. ($C_{28}H_{25}NO_9$), C.H.N.

EXAMPLE 26

4'-Demethyl-4β-[3″-fluoroanilinyl]-4-desoxypodophyllotoxin

Crystals from methanol; mp 201°-203° C. (dec).; $[α]^{25}D$-132° (c=1, $CHCl_3$); IR (KBr) 3500 (OH), 3360 (NH), 2900 (aliphatic C-H), 1750 (lactone), 1605, 1500 1475 (aromatic C=C) $cm^{-1}$; $^1HNMR$ ($CDCl_3$), δ7.15 (t, J=7.4 Hz, 1H, 5″-H), 6.76 (s, 1H, 5-H), 6.53 (s, 1H, 8-H), 6.49 (dd, H=1.2, 7.4 Hz, 1H, 4″-H), 6.40 (s, 2H, 2′, 6′-H), 6.32 (d, J=1.2 Hz, 1H, 2″-H), 6.24 (dd, J =1.2, 7.4 Hz, 1H, 6″-H), 5.97 (ABq, J=1.2, 7.9 Hz, 2H $OCH_2O$), 5.44 (s, 1H, exchangeable, 4'-OH), 4.67 (s, 1H, exchangeable, NH), 4.63 (d, J =4.0 Hz, 1H, 4-H), 4.59 (d, J=5.0 Hz, 1H, 1-H), 4.39 (t, J=8.5 Hz, 1H, 11-H) 3.98 (t, J=8.5 Hz, 1H, 11-H), 3.79 (s, 6H, 3′,5′-$OCH_3$), 3.11 (dd, J=5.0, 14.0 Hz, 1H, 2-H), 3.00 (m, 1H, 3-H). Anal. calcd for $C_{27}H_{24}FNO_7$:C,65.71;H, 4.90; N, 2.84. Found: C, 66.81; H, 4.94; N, 2.79.

EXAMPLE 27

4'-Demethyl-4β-[2″-fluoroanilinyl]-4-desoxypodophyllotoxin

Crystals from methanol; mp 197°-198° C.;$[α]^{25}D$-128° (c=0.25, $CHCl_3$); IR (KBr) 3500 (OH), 4480 (NH), 2890 (aliphatic C-H), 1755 (lactone), 1610, 1505 and (aromatic C=C) $cm^{-1}$; $^1H$ NMR ($CDCl_3$) δ7.04 (m, 2H, 3″,6″-H), 6.76 (s, 1H, 5H), 6.72 (m, 1H 5″-H), 6.60 (t, J=7.2 Hz, 1H, 4″-H), 6.54 (s, 1H, 8-H), 6.34 (s, 2H, 2′,6′-H), 5.97 (d, J=7.3 Hz, 2H, $OCH_2O$), 5.46 (s, 1H, exchangeable, 4'-OH), 4.69 (d, J=4.2 Hz, 1H, 4-H), 4.62 (d, J=4.9 Hz, 1H, 1-H), 4.38 (t, J=8.2 Hz, 1H, 11-H) 4.10 (t, 1H, exchangeable, NH), 3.82 (t, J=8.2 Hz, 1H, 11-H) 3.79 (s, 6H, 3′,5′-$OCH_3$), 3.15 (dd, J=5.0, 14.0 Hz, 1H, 2-H), 3.00 (m, 1H, 3-H). Anal. calcd for $C_{27}H_{24}FNO_7$:C,65.71;H, 4.90; N, 2.84. Found: C, 66.80; H, 4.95; N, 2.84.

EXAMPLE 28

4'-Demethyl-4β-[4″-fluoroanilinyl]-4-desoxypodophyllotoxin

Crystals from ethanol; mp 176°-177° C.;$[α]^{25}D$-100° (c=0.8, $CHCl_3$); IR (KBr) 3540 (OH), 3420 (NH), 2900 (aliphatic C-H), 1740 (lactone), 1610, 1500 1480 (aromatic C=C) $cm^{-1}$; $^1HNMR$ ($CDCl_3$) δ6.94 (t, J=6.7, 2-H, 3″,5″,-H), H), 6.75 (s, 1H, 5-H), 6.53 (s, 1H, 8H), 6.49 (q, J=2.2, 6.2 Hz, 2H, 2″,6″-H), 6.33 (s, 2H, 2′,6′-H), 5.96 (ABq, J=1.2, 7.5 Hz, 2H $OCH_2O$), 5.43 (s, 1H, exchangeable, 4'-OH), 4.60 (d, 2H, 4-H and 1-H), 4.37 (t, J=7.5 Hz, 1H, 11-H) 3.99 (t, J=7.5 Hz, 1H, 11-H), 3.79 (s, 6H, 3′,5′-$OCH_3$), 3.73 (br, 1H, exchangeable, NH), 3.13 (t, J=5.0, 14.0 Hz, 1H, 2-H), 3.00 (m, 1H, 3-H). Anal. $C_{27}H_{24}FNO_7$), C.H.N.

EXAMPLE 29

4'-Demethyl-4β-[3″,5″-difluoroanilinyl]-4-desoxypodophyllotoxin

Crystals from ethanol; mp 180°-183° C.;$[α]^{25}D$-132° (c=0.33, $CHCl_3$); IR (KBr) 3500 (OH), 3370 (NH), 2890 (aliphatic C-H), 1750 (lactone), 1620, 1590, 1500 and 1475 (aromatic C=C) $cm^{-1}$; $^1HNMR$ ($CDCl_3$) δ6.75 (s, 1H, 5-H), 6.54 (s, 1H, 8-H), 6.32 (s, 2H, 2′,6′-H), 6.23 (m, 1H, 4″-H), 6.07 (m, 2H, 2″,6″-H), 5.98 (ABq, J=1.3, 9.0 Hz, 2H $OCH_2O$), 5.45 (s, 1H, exchangeable, 4'-OH), 4.61 (m, 2H, 4-H and 1-H), 4.39 (t, J=8.5 Hz, 1H, 11-H) 4.10 (d, J=6.1 Hz, 1H, 1H, exchangeable, NH), 3.85 (t, J=8.5 Hz, 1H, 11-H), 3.81 (s, 6H, 3′,5′-$OCH_3$), 3.08 (dd, J=4.8, 14.1 Hz, 1H, 2-H), 3.02 (m, 1H, 3-H). Anal. $C_{27}H_{23}NF_2O_9$). C.H.N.

EXAMPLE 30

4'-Demethyl-4β-[3″-pyridylamino]-4-desoxypodophyllotoxin

Crystals from ethanol; mp 179°-180° (dec); $[α]^{25}_D$-99° (C=0.33, $CHCl_3$); IR (KBr) 3500 (OH), 3350 (NH), 2900 (aliphatic C-H), 1765 (lactone), 1575, 1500 and 1470 (aromatic C=C=N) $cm^{-1}$; $^1H$ NMR $CDCl_3$δ8.08 (d, J=5.5 Hz, 1H, 6″-H), 8.02 (br, 1H, 2″-H), 7.16 (m, 1H, 5″-H), 6.85 (dd, 1H, 4″-H), 6.75 (s, 1H, 5-H), 6.55 (s, 1H, 8-H), 6.32 (s, 2H, 2′, 6′H), 5.98 ($AB_q$, J=1.3, 7.3 Hz, 2H, $OCH_2O$), 4.65 (d, J=4.9 Hz, 1H, 4-H), 4.60 (m, 1H, 1-H), 4.20 (t, J=8.2 Hz, 1H, 11-H), 3.90 (m, 2H, 11-H and NH), 3.80 (s, 6H, 3′, 5′-$OCH_3$), 3.18 (dd, J=5.0, 14.1 Hz, 1H, 2-H), 3.03 (m, 1H, 3-H).

Anal. ($C_{26}H_{24}N_2O_7$) ½$H_2O$, C.H.N.

EXAMPLE 31

4'-Demethyl-4β-[2″-pyridylamino]-4-desoxypodophyllotoxin

Crystals from ethanol; mp 215°-218° (dec); $[α]^{25}_D$-82° (C=0.33, $CHCl_3$); IR (KBr) 3500 (OH), 3360 (NH), 2950 (aliphatic C-H), 1760 (lactone), 1690, 1645, 1600 and 1460 (aromatic C=C=N) $cm^{-1}$: $^1H$ NMR $CDCl_3$δ8.11 (d, 1H, 4″-H), 7.45 (m, 1H, 4″-H), 6.81 (s, 1H, 5-H), 6.67 (m, 1H, 5″-H), 6.55 (s, 1H, 8-H), 6.45 (d, 1H, 3″-H), 6.34 (s, 2H, 2′, 6′-H), 5.97 ($AB_q$, J=1.3, 6.7 Hz, 2H, $OCH_2O$), 5.43 (br, 1H, exchangeable, 4'-OH), 5.35 (m, 1H, exchangeable, NH), 4.60 (d, J=4.2 Hz, 1H, 4-H), 4.24 (m, 2H, 1-H and 11NH), 3.85 (m, 1H, 11H), 3.78 (s, 6H, 3', 5'-OCH$_3$), 3.05 (m, 2H, 2-H and 3-H). Anal. (C$_{26}$H$_{24}$N$_2$O$_7$), ½H$_2$O, C.H.N.

EXAMPLE 32

4'-Demethyl-4β-[3''-quinolinylamino]-4-desoxypodophyllotoxin

Crystals from ethanol-ether; mp 243°–246° (dec); [α]$^{25}_D$-179° (C=0.5, CHCl$_3$); IR (KBr) 3460 (OH), 3380 (NH), 2900 (aliphatic C-H), 1775 (lactone), 1605, 1510 and 1480 (aromatic C=C=N) cm$^{-1}$; $^1$H NMR CDCl$_3$δ8.46 (d, J=2.9 Hz, 2''-H), 7.97 (m, 1H, 4''-H), 7.65 (m, 1H, 7''-H), 7.48 (m, 2H, 5'', 6''-H), 6.99 (d, J=2.9 Hz, 8'-H), 6.76 (s, 1H, 5-H), 6.57 (s, 1H, 8-H), 6.35 (s, 2H, 2', 6'-H), 5.99 (AB$_q$, J=1.1, 8.0 Hz, 2H, OCH$_2$O), 5.48 (s, 1H, exchangeable, 4'-OH), 4.78 (d, J=4.8 Hz, 1H, 1-H), 4.45 (t, 1H, 11-H), 4.23 (d, 1H, exchangeable, NH), 3.99 (t, 1H, 11-H), 3.81 (s, 6H, 3', 5'-OCH$_3$), 3.15 (m, 2H, 2-H and 3-H). Anal. (C$_{30}$H$_{26}$N$_2$O$_7$), ½H$_2$O, C.H.N.

EXAMPLE 33

4'-Demethyl-4β-[3''-hydroxyanilinyl]-4-desoxypodophyllotoxin

Amorphous powder from ether: mp 163°–166° C.; IR (KBr) 3480 (OH), 3380 (NH), 2900 (aliphatic CH), 1750 (lactone), 1590, 1475 (aromatic C=C) cm$^{-1}$; $^1$NMR (CDCl$_3$) δ 7.05(t,J=8Hz,1H,5''-H), 6.78 (s,1H,5-H), 6.52(s,1H,8-H), 6.33(s,2H,2',6'-H), 6.24 (dd,J=2.2, 8Hz,1H,4''-H), 6.15(dd,J=1.7, 8HZ,1H,6''-H), 6.07(t,J=2.2Hz,1H,2''-H), 5.97(d,J=4.4Hz,2H, OCH$_2$O), 5.43(s, exchangeable), 4.82(s, exchangeable), 4.65 (d,J=3.9Hz,1H,4-H), 4.58(d,J=4.8Hz,1H,1-H), 4.37(t,J=8.7Hz,1H,11-H), 4.0(t,J=8.7Hz,1H,11-H), 3.79(s,6H,3'5'-OCH$_3$). 3.1(dd, J=4.8, 14.1 Hz, 1H, 2-H), 2.98(m,H,3-H); MS, m/z=491 (m+). Anal. Calcd for C$_{27}$H$_{25}$NO$_8$·H$_2$O: C,63.65;H,5.30. Found: C,63.35; H,5.44.

EXAMPLE 34

4'-Demethyl-4β-[2''-hydroxyanilinyl]-4-desoxypodophyllotoxin

Amorphous crystals from ether: mp 175° C.; IR (KBr) 3360 (OH, NH), 2900 (aliphatic C-H), 1750 (lactone, 1600, 1475 (aromatic C=C) cm$^{-1}$; $^1$H NMR (CDCl$_3$) δ6.88(t,J=7.4Hz,1H,4''-H), 6.78(s,1H,5-H), 6.65(m,2H,3'',6''-H), 6.5(m,2H,8-H,5''-H), 6.35(s,2H,2'6'-H), 5.96(AB$_q$ J=1.2Hz,3.5Hz,2H,OCH$_2$O), 5.44(s.exchangeable), 5.10(s, exchangeable), 4.67(d,J=4Hz,1H,4-H), 4.61(d,J=4.8Hz,1H,1-H), 4.38(t,J=8.5Hz,1H,11-H), 3.98(t,J=8.5Hz,1H,11-H), 3.79(s,6H,3',5'-OCH$_3$), 3.24 (dd,J=4.8,14Hz,1H,2-H), 3.02(m,1H,3-H), MS, m/z=491(m+). Anal. Calcd for C$_{27}$H$_{25}$NO$_8$: C,65.99; H,5.09. Found: C, 65.85; H,5.18.

EXAMPLE 35

4'-Demethyl-4β-[4''-hydroxyanilinyl]-4-desoxypodophyllotoxin

Amorphous powder from ether mp 162°–165° C.;IR (KBr) 3525 (OH), 3345 (NH), 3010 (aromatic CH), 2900 (aliphatic CH), 1745 (lactone), 1600, 1475 (aromatic C=C) cm$^{-1}$;$^1$H NMR (DMSO d$_6$, D$_2$O exchange) δ6.69(s,1H,5-H), 6.55(s,4H,2'',3'',5'',6''-H), 6.48(s,1H,8-H), 6.23(s,2H,2'6'-H), 5.94(d,J=9.7Hz,2H,O-CH$_2$-O), 4.68(d,J=4.3Hz,1H,4-H), 4.46(d,J=5.4Hz,1H,1-H), 4.29(t,J=7.6,1H,11-H), 3.76(t,J=7.6Hz,1H,11-H), 3.61(s,6H,3',5'-OCH$_3$), 3.28(dd,J=5.4,15.8Hz,1H,2-H), 2.95(m,1H,3-H).

EXAMPLE 36

4'-Demethyl-4β-[2''-chloroanilinyl]-4-desoxypodophyllotoxin

Crystals from ethyl acetate/ether, mp 253°–255° C.;[α]$^{25}$D-90° (c=1.0, CHCl$_3$); IR (KBr) 3500 (OH), 3450 (NH), 2895 (aliphatic CH), 1751 (lactone), 1590, 1500 1472 (aromatic C=C) cm$^{-1}$; $^1$H NMR (CDCl$_3$) 7.31 (dd, J=1.4, 7.9 Hz, 1H, 3''-H), 7.18 (t, J=8.8, Hz, 1H, 5''-H), 6.76 (s, 1H, 5-H), 6.73 (t, J=9.0 Hz, 4''-H) 6.58 (d, J=8.2 Hz, 1H, 6''-H), 6.54 (s, 1H, 8-H), 6.35 (s, 2H, 2',6'-H), 5.98 (ABq, J=1.2, 4.2 Hz, 2H OCOCH$_2$O), 5.44 (s, 1H, exchangeable, 4'-OH), 4.73 (t, J=4.9 Hz, 1H, 4-H) 4.64 (d, J=4.9 Hz, 1H, 1-H), 4.49 (d, J=6.0 Hz, 1H, exchangeable, NH), 4.36 (t, J=8.3 Hz, 1H, 11-H), 3.91 (t, J =8.3, Hz, 1H, 11-H), 3.80 (s, 6H, 3,'5'-OCH$_3$), 3.17 (dd, J=4.8, 14.0 Hz, 1H, 2-H), 3.04 (m, 1H, 3-H). Anal. C$_{27}$H$_{24}$ClNO$_7$ C.H.N.

EXAMPLE 37

4'-Demethyl-4β-[3''-chloroanilinyl]-4-desoxypodophyllotoxin

Crystals from ethyl acetate/ether, mp 174°–176° C.;[α]$^{25}$D-112° (C=1.0, CHCl$_3$); IR (KBr) 3500 (OH), 3360 (NH), 2920 (aliphatic CH), 1752 (lactone), 1580, and 1452 (aromatic C=C) cm$^{-1}$; $^1$H NMR (CDCl$_3$) 7.12 (t, J=8.1, Hz, 1H, 5''-H), 6.76 (s, 1H, 5-H), 6.74 (dd, J=1.0, 8.1 Hz, 1H 4''-H), 6.53 (br, 2H, 8-H and 2''-H), 6.42 (dd, J=1.6, 6.5 Hz, 1H, 6''-H), 6.33 (s, 2H, 2',6'-H), 5.97 (ABq, J=1.0, 8.7 Hz, 2H OCH$_2$O) 5.43 (s, 1H, exchangeable, 4'-OH), 4.66 (br, 1H, 4-H), 4.59 (d, J=4.8 Hz, 1H, 1-H), 4.39 (t, J=7.7 Hz, 1H, 11-H), 3.99 (t, J=7.7 Hz, 1H, 11-H) 3.96 (br, 1H, exchangeable, NH), 3.79 (s, 6H, 3, '5'-OCH$_3$), 3.11 (dd, J=5.8, 14.0 Hz, H, 2-H), 3.01 (m, 1H, 3-H). Anal. C$_{27}$H$_{24}$ClNO$_7$), C.H.N.

EXAMPLE 38

4'-Demethyl-4β-[4''-chloroanilinyl]-4-desoxypodophyllotoxin

Crystals from ethyl acetate/ether, mp 253°–255° C.;[α]$^{25}$D-125° (c=0.75 CHCl$_3$); IR (KBr) 3500 (OH), 3360 (NH), 2920 (aliphatic CH), 1758 (lactone), 1605, 1590 and 1475 (aromatic C=C) cm$^{-1}$; $^1$H NMR (CDCl$_3$) δ7.17 (d, J=8.7, Hz, 2H, 3'',5''-H), 6.74 (s, 1H, 5-H), 6.53 (s, 1H, 8-H), 6.48 (d, J=8.7 Hz, 2H, 2'',6''-H), 6.32 (s, 2'6'-H), 5.96 (ABq, J=1.0, 6.8 Hz, 2H OCH$_2$O), 5.43 (s, 1H, exchangeable, 4'-OH), 4.63 (d, J=4.2 Hz, 1H, 4-H), 4.59 (d, J=4.9 Hz, 1H, 1-H), 4.38 (t, J=8.0 Hz, 1H, 11-H) 3.96 (t,J=8.0 Hz, 1H, 11-H), 3.79 (s, 6H 3,'5'-OCH$_3$), 3.12 (dd, J=4.9, 14.1 Hz, H, 2-H), 2.99 (m, 1H, 3-H). Anal. C$_{27}$H$_{24}$ClNO$_7$), C.H.N.

EXAMPLE 39

4'-Demethyl-4β-[3''-bromoanilinyl]-4-desoxypodophyllotoxin

Crystals from methanol/ether; mp 177°–179° C.;[α]$^{25}$D-105° (c=1, CHCl$_3$); IR (KBr) 3450 (OH), 3340 (NH), 2900 (aliphatic CH), 1740 (lactone), 1590, 1500 and 1475 (aromatic C=C) cm$^{-1}$; $^1$H NMR (CDCl$_3$) δ7.07 (t, J=8.0, Hz, 1H, 5''-H), 6.90 (dd, J=0.9, 7.9 Hz, 1H, 4''-H), 6.75 (s, 1H, 5-H), 6.70 (br, 1H, 2''-H), 6.53 (s, 1H, 8-H), 6.47 (dd, J=1.7, 8.3 Hz, 1H 6''-H), 6.33 (s, 2H, 2',6'-H), 5.97 (dd, J=1.2, 9.3 Hz, 2H, OCH$_2$O), 5.43 (s, 1H, exchangeable, 4'-OH), 4.65 (d, J=4.2 Hz, 1H, 4-H), 4.60 (d, J=4.8 Hz, 1-H), 4.39 (t, J=7.3 Hz, 1H, 11-H) 3.96 (t, J=7.3 Hz, 1H, 11-H), 3.90 (d, J=6.2, Hz, 1H, exchangeable, NH), 3.80 (s, 6H, 3',5'-OCH$_3$), 3.10 (dd, J=4.9, 14.0 Hz, 1H, 2-H), 3.02 (m, 1H, 3-H). Anal. C$_{27}$H$_{24}$BrNO$_7$), C.H.N.

EXAMPLE 40

4'-Demethyl-4β-[4''-bromoanilinyl]-4-desoxypodophyllotoxin

Crystals from ethyl acetate/ethanol; mp 227°–230° C.;[α]$^{25}$D-110° (c=0.5, CHCl$_3$); IR (KBr) 3500 (OH), 3330 (NH), 2900 (aliphatic CH), 1755 (lactone), 1605, 1590 and 1475 (aromatic C=C) cm$^{-1}$; $^1$H NMR (CDCl$_3$) δ7.30 (d, J=8.9, Hz, 2H, 3'',5''-H), 6.75 (s, 1H, 5-H), 6.53 (s, 1H, 8-H), 6.44 (d, J=8.9 Hz, 2H, 2'',6''-H), 6.32 (s, 2H, 2',6'-H), 5.98 (ABq, J=1.3, 8.3 Hz, 2H, OCH$_2$O), 5.42 (s, 1H, exchangeable, 4'-OH), 4.62 (m, 2H, 4-H and 1-H), 4.36 (t, J=8.5 Hz, 1H, 11-H), 3.95 (t, 8.5 Hz, 11-H), 3.86 (d, J=7.8, 1H, exchangeable, NH), 3.79 (s, 6H, 3,'5'-OCH$_3$), 3.11 dd, J=4.8, 14.1 Hz, 1H, 2-H), 3.00 (m, 1H, 3-H). Anal. C$_{27}$H$_{24}$BrNO$_7$) C.H.N.

EXAMPLE 41

4'-Demethyl-4β-[4''-iodoanilinyl]-4-desoxypodophyllotoxin

Crystals from ethanol; mp 198°–200° C. (dec.);[α]$^{25}$D-111° (c=0.5, CHCl$_3$); IR (KBr) 3540 (OH), 3420 (NH), 2900 (aliphatic CH), 1770 (lactone), 1610, 1585 and 1480 (aromatic C=C) cm$^{-1}$; $^1$H NMR (CDCl$_3$) δ7.46 (d, J=8.8 Hz, 2H, 2'',6''-H), 6.32 (s, 2H, 2',6'-H), 5.59 (ABq, J=1.1, 8.9 Hz, 2H, OCH$_2$O), 5.44 (s, 1H, exchangeable, 4'-OH), 4.62 (m, 1H, 4-H), 4.58 (d, J=4.9 Hz, 1H, 1-H), 4.34 (t, J=8.5 Hz, 1H, 11-H), 3.94 (m, 2H, 11-H and NH), 3.78 (s, 6H, 3',5'-OCH$_3$), 3.09 (dd, J=4.9, 14.1 Hz, 1H, 2-H), 2.99 (m, 1H, 3-H). Anal. C$_{27}$H$_{24}$BrNO$_7$), C.H.N.

EXAMPLE 42–44

(Scheme IX)

Podophyllotoxin (500 mg, 1.2 mmol) was dissolved in dry dichloromethane (10 ml) and kept at 0° C. Hydrogen bromide gas was introduced into the solution for 45 min., after which time the solvent was evaporated in vacuo, anhydrous tetrahydrofuran (15 ml), anhydrous barium carbonate (474 mg, 2.4 mmol) and the appropriate hydroxyaniline (142mg, 1.3 mmol) was added. The mixture stood at room temperature overnight, and then was filtered and concentrated. The crude product was purified using column chromatography (silica gel 45 g with dichloromethane-acetone-ethyl acetate 100:5:5 as an eluant). The products (42–44) obtained in the examples had the characteristics listed below.

EXAMPLE 42

4β-[2''-hydroxyanilinyl]-4-desoxypodophyllotoxin

Amorphous crystals from ether: mp 145-148° C.; IR (KBr) 3480 (OH), 3410 (NH), 2900 (aliphatic CH), 1760 (lactone), 1580, 1475 (aromatic C=C) cm$^{-1}$; H NMR (CDCl$_3$) δ6.90 (t,J=6.6 Hz, 1H, 4''-H), 6.78 (s, 1H, 5-H), 6.65 (m, 2H, 3'',6''-H), 6.53 (m, 2H,8-H, 5''-H), 6.34 (s, 2H 2',6'-H), 5.96 (ABq, J=1.0, 3.5 Hz,2H, OCH$_2$O), 5.02 (s, 1H, exchangeable, 2''-OH), 4.68 (m, 1H, 4-H), 4.62 (d, J=4.9 Hz, 1H, 1-H), 4.38 (t, J=8.6 Hz, 1H, 11-H), 4.33 (m, 1H, exchangeable, NH), 4.00 (t, J=8.6 Hz, 1H, 11H), 3.82 (s, 3H, 4'-OCH$_3$), 3.76 (s, 6H, 3',5'-OCH$_3$), 3.25 (dd, J=5.1, 14.0 Hz, 1H, 2-H), 3.05 (m, 1H, 3-H). MS, m/z=505 (m+). Anal. (C$_{28}$H$_{27}$NO$_8$3/2 H$_2$O) C.H.

EXAMPLE 43

4β-[3''-hydroxyanilinyl]-4-Desoxypodophyllotoxin

Amorphous powder from ether, mp 148°–150° C.; IR(KBr) 3370 (OH,NH), 2900 (aliphatic CH), 1760 (lactone), 1585, 1475 (aromatic C=C) cm$^{-1}$; $^1$H NMR (CDCl$_3$) δ7.05 (t, J=8.0 Hz, 1H, 5''-H), 6.77 (s, 1H, 5H), 6.52 (s, 1H, 8-H), 6.32 (s, 2H, 2'6'-H), 6.25 (dd, J=2.2, 8.0 Hz, 1H, 4''-H), 6.14 (dd, J=2.2, 8.0 Hz, 1H, 6''-H), 6.05 (t=2.2 Hz, 1H, 2''-H), 5.96 (ABq, J=1.3, 3.8 Hz, 2H OCH$_2$O), 4.64 (d, J=3.9 1H, 4-H), 4.49 (d, J=5.0, Hz, 1H, 1-H), 4.4 (t, J=8.7 Hz, 1H, 11-H), 4.03 (t, J=8.7 Hz, 1H, 11-H), 3.81 (s, 3H, 4'OCH$_3$), 3.76 (s, 6H, 3',5'-OCH$_3$), 3.18 (s, 6H, 3',5'-OCH$_3$), 3.18 (dd, J=5.0 Hz, 4.0 Hz, 1H,2-H), 3.02 (m, 1H, 3-H); MS, m/z=505 (m+). Anal. (C$_{28}$H$_{27}$NO$_8$ H$_2$O) C.H.

EXAMPLE 44

4β-[4''-hydroxyanilinyl]-4-desoxypodophyllotoxin

Crystals from chloroform; mp 145°–150° C.; IR(KBr) 3310 (OH,NH), 3010 (aromatic CH), 2900 (aliphatic CH), 1730 (latone), 1575, 1475 (aromatic C=H) cm$^{-1}$; $^1$H NMR (CDCl$_3$) D$_2$O exchange) δ 6.75 (d, J=8.3 Hz, 3H, 5-H, 3'',5''-H), 6.53 (s, 1H, 8H), 6.45 (d, J=8.3 Hz, 2H, 2'',6''-H), 6.23 (s, 2H 2'6'-H), 5.95 (ABq, J=1.0, 4.0 Hz, 2H OCH$_2$O), 4.60 (d, J=4.2 Hz, 1H, 4-H), 4.57 (d, J=4.6 Hz, 1H, 1-H), 4.38 (t, J=6.0 Hz, 1H, 11-H), 4.05 (t, J=6.0 Hz, 1H, 11H) 3.83 (s, 3H, 4-OCH$_3$), 3.75 (s, 6H, 3',5'-OCH$_3$), 3.18 (dd, J=4.6 Hz, 14.0 Hz, 1H,2-H), 3.0 (m, 1H, 3-H).

Anal. (C$_{28}$H$_{27}$NO$_8$ ½H$_2$O) C.H.

Isolation of Human DNA Topoisomerase II

Human DNA topoisomerase II was isolated from peripheral blast cells of a patient with acute leukemia. The isolation procedure is described in Thurston, L., Imakura, Y., Haruna, M., Li, Z. C., Liu, S. Y., and Lee, K. H., *J. Med. Chem.*, 31, COMPLETE (1988) and is a partial combination of the procedure described in Goto, T., Laiapia, P. and Wang, J., *J. Biol. Chem.*, 259, 10422 (1984) and Halligan, B., Edwards, K., and Liu, L., *J. Biol. Chem..* 260, 2475 (1985) which are herein specifically incorporated by reference.

Preparations of Drugs

Drugs were dissolved in Me$_2$SO at a concentration of 20 mM as the stock solution and diluted before use with water to the desired concentration of each drug.

DNA Topoisomerase II Assay

The P4 unknotting reaction was a modification of the procedure described by Hseih, T., *J. Biol. Chem.*, 258, 8413 (1985), which is herein specifically incorporated by reference.

The reaction mixture (20 μL), which contained 50 mM HEPES, pH 7.0, 50 mM KCl, 100 mM NaCl, 0.1 mM EDTA, 10 mM MgCl$_2$, 1.0 mM ATP, 50 μg/mL bovine serum albumin, 0.4 μg P4 knotted DNA, and enzyme, was incubated with or without drugs.

The reaction mixture was incubated at 37° C. for 30 min and terminated by adding 5.0 μl of a stop solution (2% sodium dodecyl sulfate, 20% glycerol, 0.05% bromophenol blue). These samples were loaded onto a 1% agarose gel and electrophoresed at 55 V overnight with an electrophoresis buffer that contained 90 mM Trisboric acid, pH 8.3, and 2.5 mM EDTA. At completion, the gel was stained in 0.5 μg/mL of ethidium bromide. Then a photograph was taken of the DNA bands visualized with fluorescence induced by a long-wavelength UV lamp. The data reported in Table 1 reflect a 100 μM drug concentration.

K-SDS Precipitation Assay for Protein-DNA Complexes

The intracellular formation of covalent topoisomerase II-DNA complexes was quantitated using the potassium SDS precipitation assay, a procedure adapted from the method described in Rowe, T.C., Chen, G. L., Hsiang, Y. H., and Liu, L., Cancer Res., 46, 2021 (1986) (hereinafter Rowe et al.), which is herein specifically incorporated by reference. KB ATCC cells were prelabeled with 0.05 mCi/ml $^{14}$C-thymidine (specific activity 50.5 mCi/mmol) for 18 hr. A final concentration of $5 \times 10^5$ cells/sample were treated with 10 μM of the drugs at 37° C. for 1 hr and proceeded according to the procedure described by Rowe et al. to detect the protein-linked DNA levels.

It will be apparent to those skilled in the art that various modifications and variations can be made in the processes and products of the present invention. Thus, it is intended that the present invention cover the modifications and variations of this invention provided that they come within the scope of the appended claims and their equivalents.

TABLE I

BIOLOGICAL EVALUATION OF 4'-DEMETHYL-4-ALKYLAMINO-PODOPHYLLOTOXIN ANALOGUES

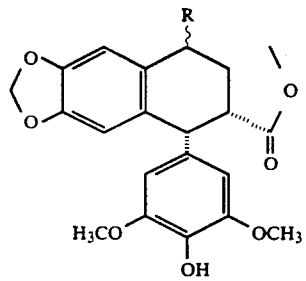

| COMPOUND | R | CYTOTOXICITY[a] ED$_{50}$KB (μg/ml) | DNA TOPO-ISOMERASE II ACTIVITY % INHIBITION[b] | CELLULAR PROTEIN-DNA COMPLEX FORMATION[c] % |
|---|---|---|---|---|
| Etoposide | | 0.20 | +++ | 100.0 |
| Example: | | | | |
| 1 | β-OH | 0.34 | ++ | 42.2 |
| 2 | α-OH | 0.045 | + | 3.3 |
| 3 | β-NH$_2$ | 1.0 | ++++ | 36.4 |
| 4 | α-NH$_2$ | 0.42 | + | 8.0 |
| 5 | β-NHCH$_2$CH$_2$OH | 1.6 | ++++ | 121.4 |
| 6 | α-NHCH$_2$CH$_2$OH | 710.0 | − | 0.0 |
| 7 | β-NHCH$_2$CH$_2$CH$_3$ | <0.4 | ++ | 69.7 |
| 8 | β-NHCH$_2$CH$_2$OCH$_3$ | >4.0 | +++ | 110.8 |
| 9 | β-NHCH$_2$CH=CH$_2$ | 3.4 | +++ | 84.1 |
| 10 | β-NHCH$_2$CH(OH)CH$_3$ | 3.6 | ++++ | 167.2 |
| 11 | β-NHCH(CH$_3$)CH$_2$OH | 2.3 | ++++ | 161.7 |
| 12 | β-NHCH$_2$CH$_2$CH$_2$OH | 4.0 | ++ | 89.2 |
| 13 | β-OCH$_2$CH$_2$NH$_2$ | 0.1 | ++++ | 300.0 |
| 14 | β-OCH$_2$CH$_2$OH | 0.7 | ++ | 50.0 |

[a]ED$_{50}$ is the concentration of drug which affords 50% reduction in cell number after 3 days incubation.
[b]+, ++, +++, ++++ and − denote for 25%, 50%, 75%, >75%, and 0% inhibition.
[c]Relative activities of cellular protein-DNA complex formation in KB ATCC tissue culture cells measured at 10 μM drug concentration as compared the complex formed by 10 μM of etoposide.

TABLE II

COMPOUNDS WITH POTENT TOPOISOMERASE II INHIBITORY ACTIVITY

| TOPOISOMERASE II COMPOUNDS | DNA TOPOISOMERASE INHIBITORY ACTIVITY[a] (RELATIVE POTENCY) |
|---|---|
| Etoposide | 1.0 |
| 15 | 2.0–6.0 |
| 16 | 8.0 |
| 17 | 2.0 |
| 18 | 2.0 |

TABLE II-continued
COMPOUNDS WITH POTENT TOPOISOMERASE II INHIBITORY ACTIVITY

| TOPOISOMERASE II COMPOUNDS | DNA DNA TOPOISOMERASE INHIBITORY ACTIVITY[a] (RELATIVE POTENCY) |
|---|---|
| 15 | R = Cl |
| 16 | $R_1 = R_2 = R_3 = R_5 = Br, R_4 = H$ |
| 17 | $R_1 = OH, R_2 = R_4 = R_5 = Br, R_3 = H$ |
| 18 | $R_1 = OH, R_2 = R_3 = R_4 = R_5 = Br$ |

[a]Several different concentrations of tested compounds were employed for the determination of their potency. The relative potency with respect to etoposide as expressed in Table I was the relative concentration of compounds tested to achieve the same degree inhibition by etoposide in the range of 25 to 400 μM.

TABLE III
Biological Evaluation of 4-Demethyl-4β(arylamino)-4-desoxy Podopyllotoxin

| Compound | $R_1$ | DNA Topoisomerase II Activity % Inhibition[b] | Cellular Protein-DNA Complex Formation[c] | Cytotoxicity $ID_{50}$ $K_B$ $(uM)^d$ |
|---|---|---|---|---|
| Etoposide | | +++ | 100 | 0.2 |
| 19 | NH—C₆H₅ | +++ | 243 | 0.71 |
| 20 | NH—C₆H₄—CH | ++++ | 211 | 0.64 |
| 21 | NH—C₆H₄—CH (meta) | +++ | 137 | 0.69 |
| 22 | NH—C₆H₄—CO₂C₂H₅ | +++ | 207 | <0.10 |

TABLE III-continued
Biological Evaluation of 4-Demethyl-4β(arylamino)-4-desoxy Podopyllotoxin
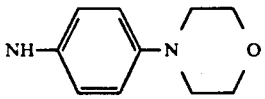
| Compound | R₁ | DNA Topoisomerase II Activity % Inhibition[b] | Cellular Protein-DNA Complex Formation[c] | Cytotoxicity ID$_{50}$ K$_B$ (uM)[a] |
|---|---|---|---|---|
| 23 | 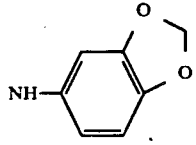 | +++ | 140 | 0.66 |
| 24 | 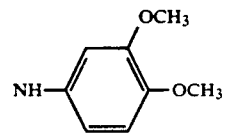 | ++++ | 164 | <1.0 |
| 25 | 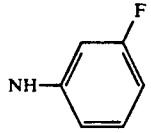 | ++ | 180 | <1.0 |
| 26 | 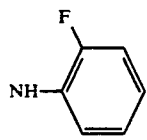 | +++ | 158 | 0.23 |
| 27 | 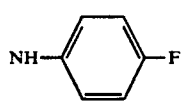 | ++ | 121 | 0.25 |
| 28 | 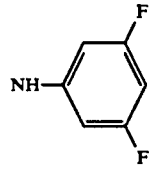 | ++++ | 213 | 0.24 |
| 29 | 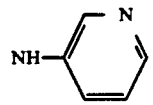 | ++ | 115 | 1.08 |
| 30 | 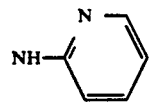 | +++ | 148 | 0.24 |
| 31 |  | ++ | 97 | 0.71 |

TABLE III-continued
Biological Evaluation of 4-Demethyl-4β(arylamino)-4-desoxy Podopyllotoxin
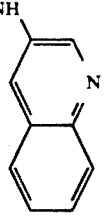
| Compound | R₁ | DNA Topoisomerase II Activity % Inhibition[b] | Cellular Protein-DNA Complex Formation[c] | Cytotoxicity ID$_{50}$ K$_B$ (uM)[a] |
|---|---|---|---|---|
| 32 | 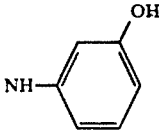 | + + | 123 | <1.0 |
| 33 | 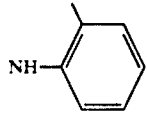 | + + + + | 290 | 0.45 |
| 34 | 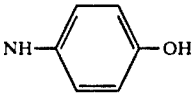 | + + + + | 151 | 4.54 |
| 35 | 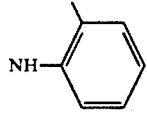 | + + + | 211 | 2.26 |
| 36 | 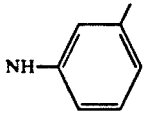 | + | 32 | 2.34 |
| 37 | 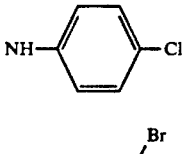 | + + | 51 | 2.29 |
| 38 | 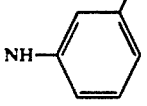 | + + + | 99 | 0.22 |
| 39 |  | + | 62 | 2.36 |

TABLE III-continued

Biological Evaluation of 4-Demethyl-4β(arylamino)-4-desoxy Podopyllotoxin

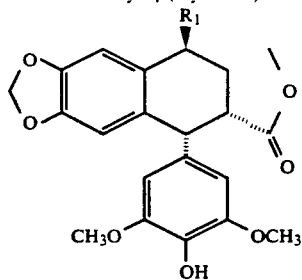

| Compound | R₁ | DNA Topoisomerase II Activity % Inhibition[b] | Cellular Protein-DNA Complex Formation[c] | Cytotoxicity ID$_{50}$ K$_B$ (uM)[a] |
|---|---|---|---|---|
| 40 | NH—⟨⟩—Br | ++ | 179 | 0.22 |
| 41 | NH—⟨⟩—I | + | 64 | 0.34 |

[a] ID$_{50}$ is the concentration of drug which affords 50% reduction in cell number after 3 days incubation.
[b] Activities of cellular protein-DNA complex formation in KB ATCC tissue culture cells relative to Etoposide.
[c] +, ++, +++, ++++ denote 0-24%, 25-49%, 50-74%, and ≧75% inhibition respectively.

TABLE IV

Biological Evaluation of 4β-(arylamino)-4-desoxypodophyllotoxins

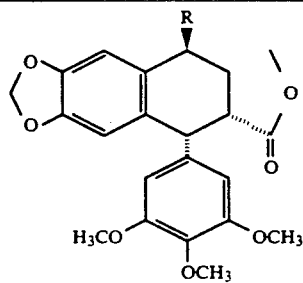

| Compound | R | DNA Topoisomerase II Activity % Inhibition | Cellular protein-DNA Complex Formation | Cytotoxicity ID$_{50}$KB (μM) |
|---|---|---|---|---|
| Etoposide | | +++ | 100 | 0.2 |
| 42 | NH—⟨⟩-OH (ortho) | + | 6 | 4.11 |
| 43 | NH—⟨⟩-OH (meta) | + | 37 | 0.31 |
| 44 | NH—⟨⟩—OH (para) | + | 21 | 0.31 |

Scheme I
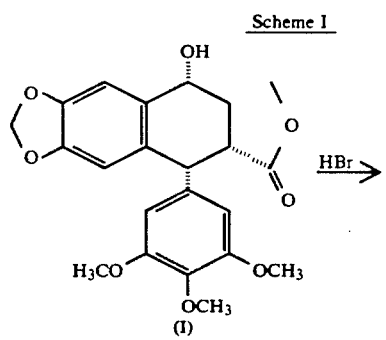
(I)
HBr →
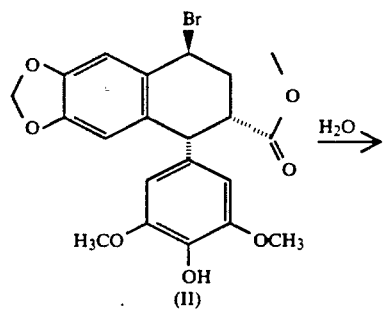
(II)
H₂O →
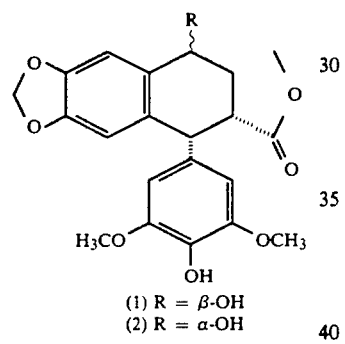
(1) R = β-OH
(2) R = α-OH
Scheme II
CBz—Cl ↓
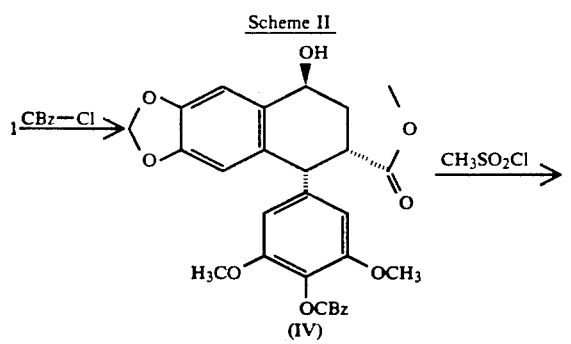
(IV)
CH₃SO₂Cl →
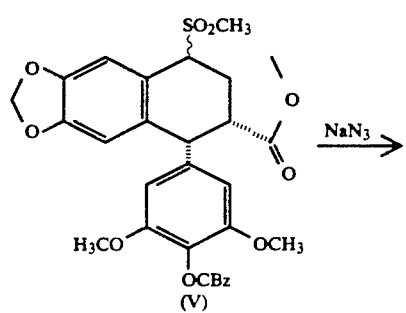
(V)
NaN₃ →
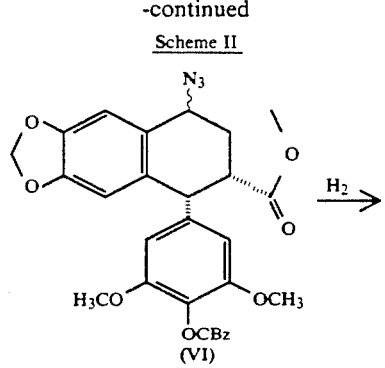
(VI)
H₂ →
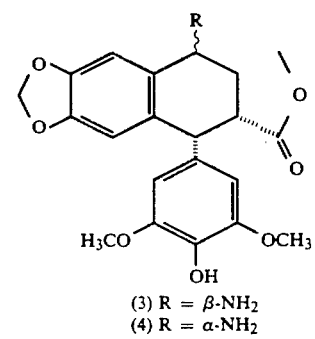
(3) R = β-NH₂
(4) R = α-NH₂
Scheme III
II $\xrightarrow{RNH_2}$
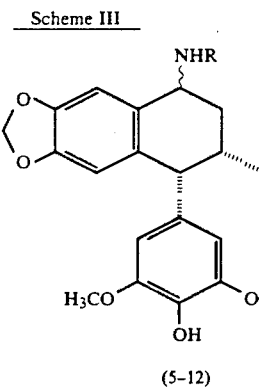
(5–12)
Scheme IV
II $\xrightarrow{HOCH_2CH_2Br}$
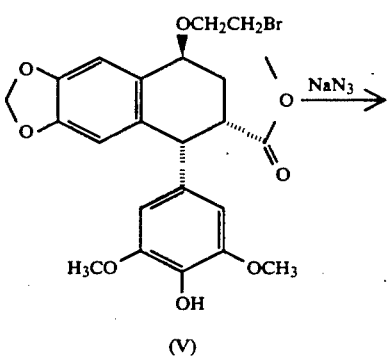
(V)
NaN₃ →

Scheme IV -continued
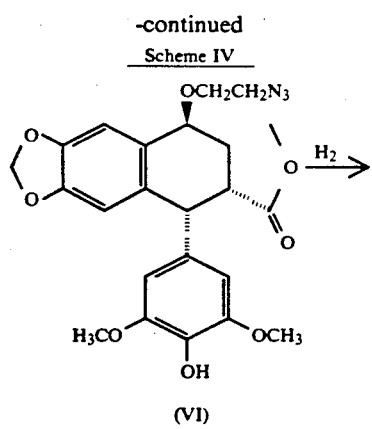
(VI)
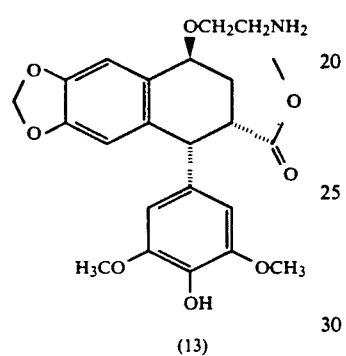
(13)
Scheme V
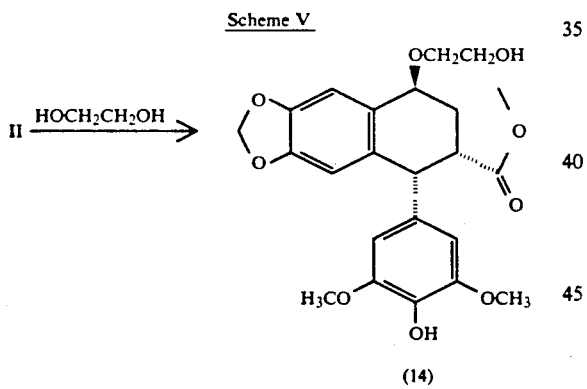
(14)
Scheme VI
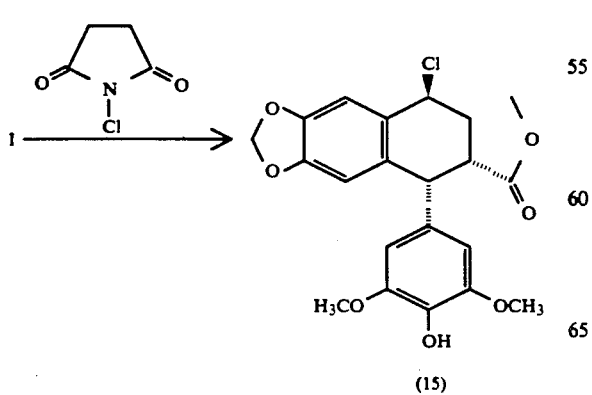
(15)
Scheme VII
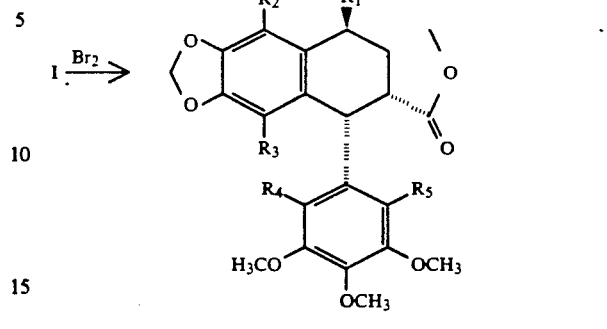
(16) $R_1 = R_2 = R_3 = R_5 = Br, R_4 = H$
(17) $R_1 = OH, R_2 = R_4 = R_5 = Br, R_3 = H$
(18) $R_1 = OH, R_2 = R_3 = R_4 = R_5 = Br$
Scheme VIII
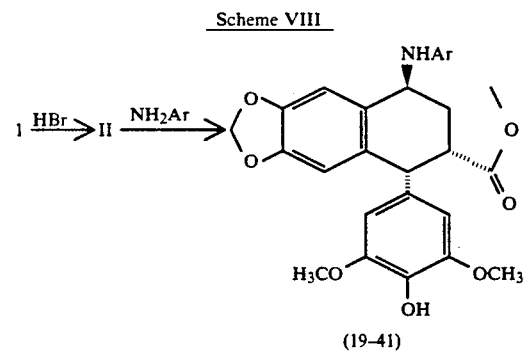
(19–41)
Scheme IX
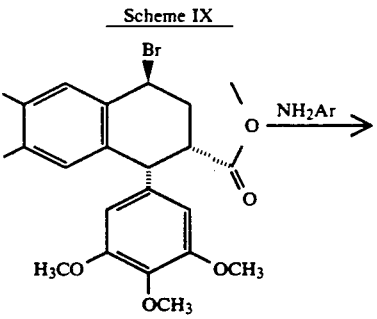
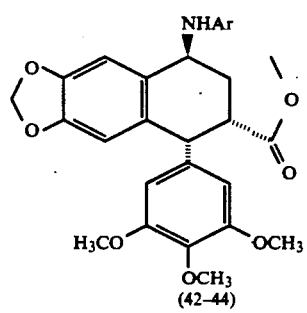
(42–44)
What is claimed is:
1. A compound having the formula:

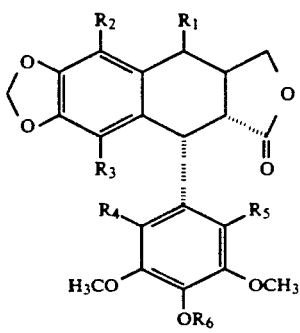

where:
R₁ is β-NHCH(CH₃)CH₂OH, β-NHCH₂CH(CH₃)OH, β-NHCH₂CH₂OH, α-NHCH₂CH₂OH, β-NHCH₂CH₂CH₃, β-NHCH₂CH₂OCH₃, β-NHCH₂CH=CH₂, β-NHCH₂CH(OH)CH₃, β-NHCH₂CH₂CH₂OH; or β-OCH₂CH₂OH;
wherein R₁ is

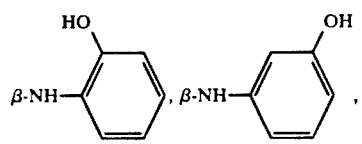

R₂ is H, or Br;
R₃ is H, or Br;
R₄ is H, or Br;
R₅ is H, or Br; and
R₆ is H, or —CH₃.

2. A compound having the formula:

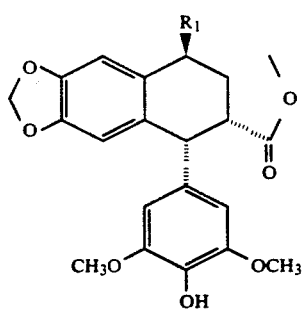

where R₁ is —NHCCH₃HCH₂OH, —NHCH₂CCH₃HOH, or NHR₈, wherein R₈ is

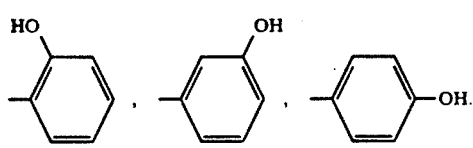

3. A compound having the formula:

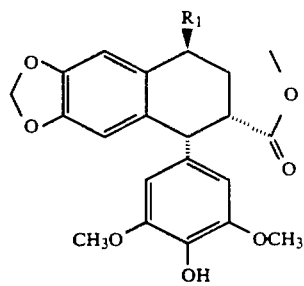

where R₁ is —NHCH₂CH₂OH.

4. A pharmaceutical composition comprising a compound having antitumor activity of the formula:

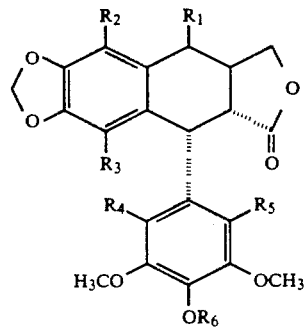

where:
R₁ is β-NHCCH₃HCH₂OH, β-NHCH₂CCH₃HOH, β-NHCH₂CH₂OH, α-NHCH₂CH₂OH, β-NHCH₂CH₂CH₃, β-NHCH₂CH₂OCH₃, β-NHCH₂CH=CH₂, β-NHCH₂CH(OH)CH₃, β-NHCH₂CH₂CH₂OH, β-OCH₂CH₂OH;
wherein R₁ is

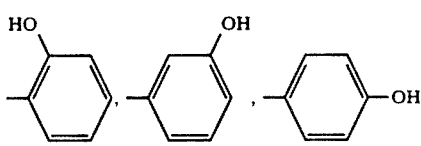

R₂ is H, or Br;
R₃ is H, or Br;
R₄ is H, or Br;
R₅ is H, or Br; and
R₆ is H, or —CH₃.

5. A compound according to claim 1 exhibiting antitumor activity.

6. A compound of the formula:

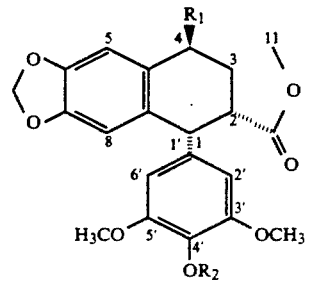

where R₁ is

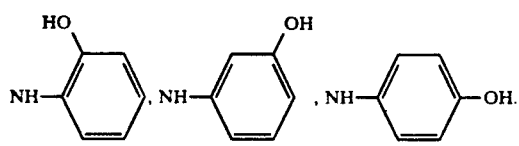
and R$_2$ is CH$_3$.
7. A pharmaceutical composition comprising a compound having the formula:
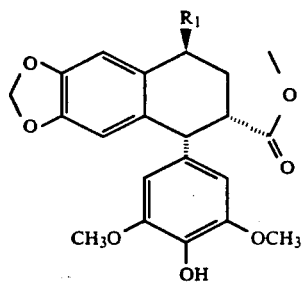
where R$_1$ is selected from:
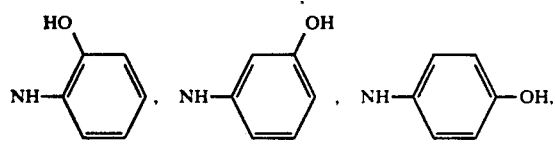
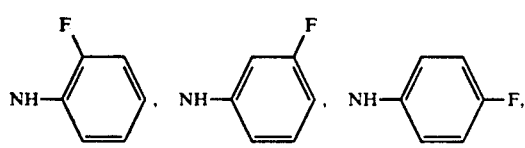
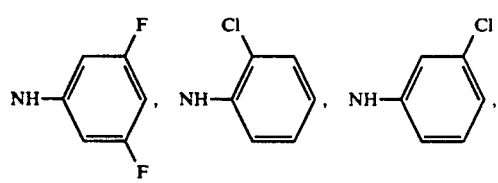
-continued
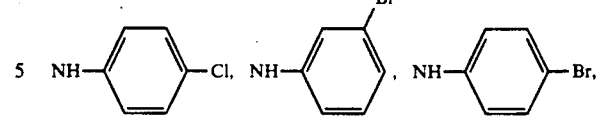
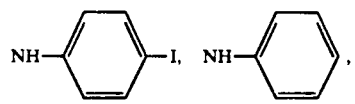
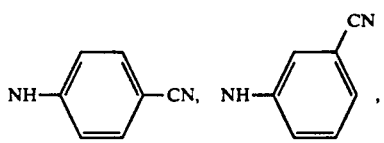
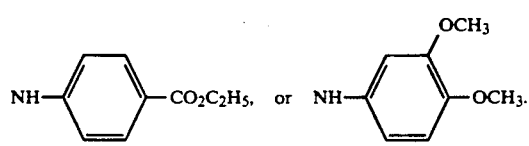
8. A compound of the formula:
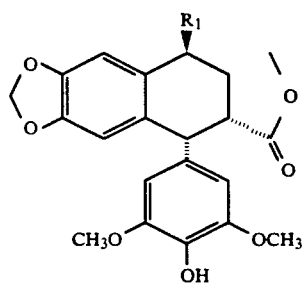
wherein R$_1$ is
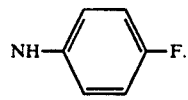
9. A pharmaceutical composition comprising the compound of claim 8, and a pharmaceutically acceptable carrier.
* * * * *

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

IN THE ABSTRACT

In the Abstract, that portion of the formula reading

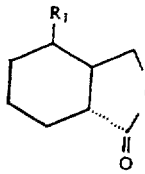   should read   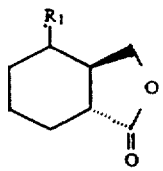

IN THE SPECIFICATION

Column 1, lines 17-37, that portion of the formula reading

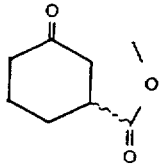   should read   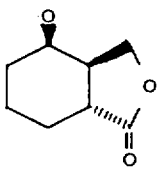

Column 4, lines 34-43, that portion of the formula reading

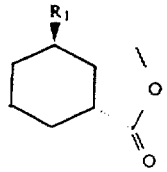   should read   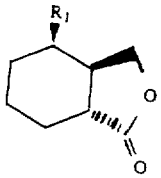

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

```
Column 5, lines 7-8, replace "4'-Demethyl" with --4'-O-Demethyl--;
         lines 8-9, replace "4'-Demethyl" with --4'-O-Demethyl--;
         line 10, replace "4'-Demethyl" with --4'-O-Demethyl--;
         line 11, replace "4'-Demethyl" with --4'-O-Demethyl--;
         lines 13-14, replace "4'-demethyl" with --4'-O-Demethyl--;
         lines 14-15, replace "4'-Demethyl" with --4'-O-Demethyl--;
         line 16, replace "4'-Demethyl" with --4'-O-Demethyl--;
         line 17, replace "4'-Demethyl" with --4'-O-Demethyl--;
         line 18, replace "4'-Demethyl" with --4'-O-Demethyl--;
         lines 19-20, replace "4'-Demethyl" with --4'-O-Demethyl--;
         line 21, replace "4'-Demethyl" with --4'-O-Demethyl--;
         line 22, replace "4'-Demethyl" with --4'-O-Demethyl--;
         line 23, replace "4'-Demethyl" with --4'-O-Demethyl--;
         lines 24-25, replace "4'-Demethyl" with --4'-O-Demethyl--;
```

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

line 26, replace "4'-Demethyl" with --4'-O-Demethyl--;
line 27, replace "4'-Demethyl" with --4'-O-Demethyl--;
line 28, replace "4'-Demethyl" with --4'-O-Demethyl--;
line 29, replace "4'-Demethyl" with --4'-O-Demethyl--;
line 31, replace "4'-Demethyl" with --4'-O-Demethyl--;
line 32, replace "4'-Demethyl" with --4'-O-Demethyl--;
lines 33-34, replace "4'-Demethyl" with --4'-O-Demethyl--;
line 35, replace "4'-Demethyl" with --4'-O-Demethyl--;
line 36, replace "4'-Demethyl" with --4'-O-Demethyl--; and
lines 52-63, that portion of the formula reading

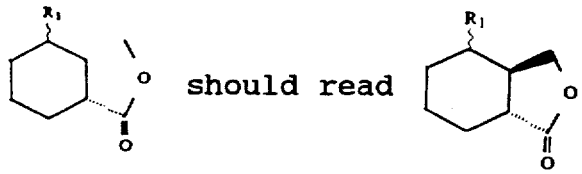

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

Column 7, lines 23-34, that portion of the formula reading 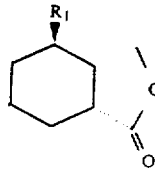 should read 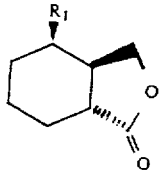

Column 8, lines 1-13, that portion of the formula reading 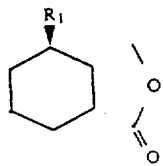 should read 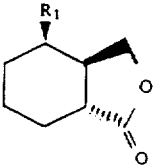

Column 8, lines 51-61, that portion of the formula reading 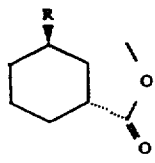 should read 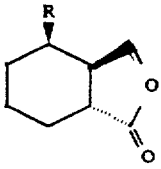

Column 16, line 35, replace "ß-desocypodophyllotoxin" with --ß-desoxypodophyllotoxin--.

Column 17, line 17, replace "4'demethyl" with --4'-demethyl--.

Column 18, line 22, replace "d, J = 7.0" with --ABq, J = 1.3 --.

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

Column 18, line 58, replace "d, J = 66.7" with --br.--;
        line 62, after "3-H and 4-H," insert --morpholino,--.

Column 19, line 29, replace "d, J = 2.4 Hz" with --ABq, J = 1.2, 7.0--; and
        line 65, replace "d, J = 7.3" with --ABq, J = 1.2, 7.3--.

Column 21, line 32, delete "d, J = 4.4 Hz".

Columns 25 and 26, TABLE I, that portion of the formula reading

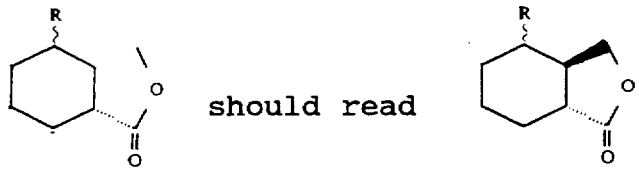

Column 27, TABLE II, "TOPOISOMERASE II COMPOUNDS," that portion of the formula reading

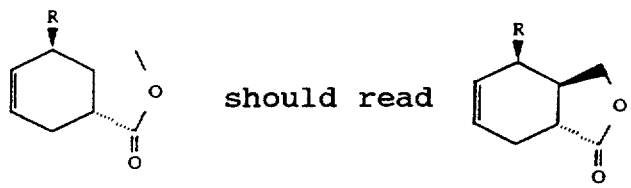

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

Column 27, TABLE II, "DNA TOPOISOMERASE INHIBITORY ACTIVITY," that portion of the formula reading

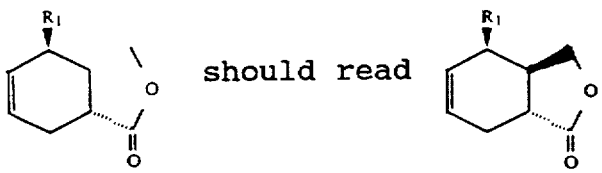

Column 27, TABLE III, that portion of the formula reading

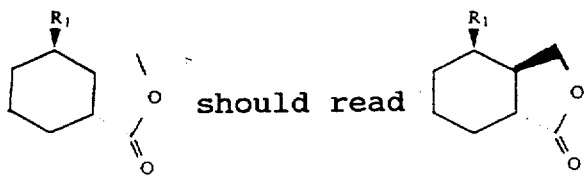

Column 27, TABLE III, Etoposide 20, that portion of the formula reading

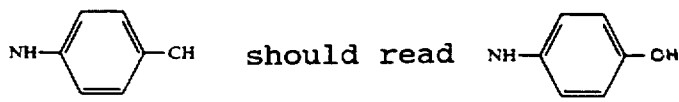

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

Column 27, TABLE III, Etoposide 21, that portion of the formula reading

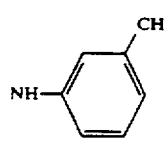   should read   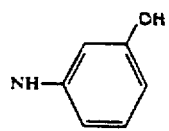

Column 29, TABLE III, that portion of the formula reading

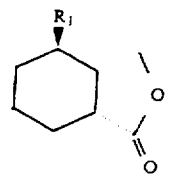   should read   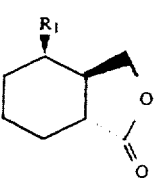

Column 31, TABLE III, that portion of the formula reading

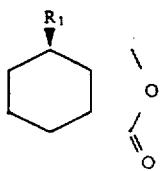   should read   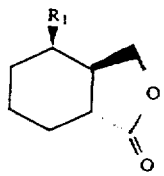

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

Column 35, lines 16-26, that portion of the formula reading

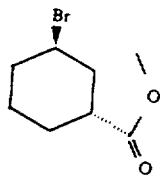    should read    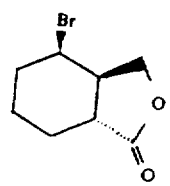

Column 35, lines 28-40, that portion of the formula reading

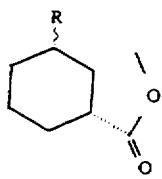    should read    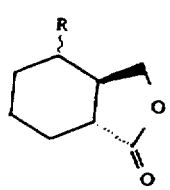

Column 35, lines 44-54, that portion of the formula reading

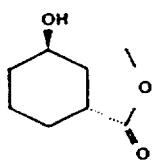    should read    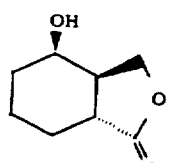

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

Column 35, lines 57-67, that portion of the formula reading

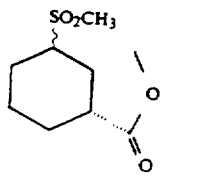   should read   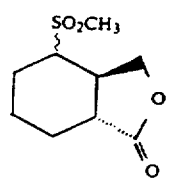

Column 36, lines 5-15, that portion of the formula reading

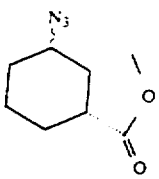   should read   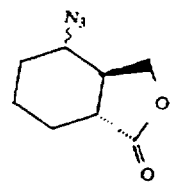

Column 36, lines 18-29, that portion of the formula reading

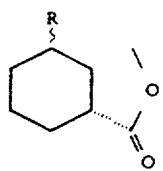   should read   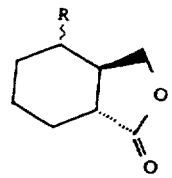

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

Column 33, TABLE III, that portion of the formula reading

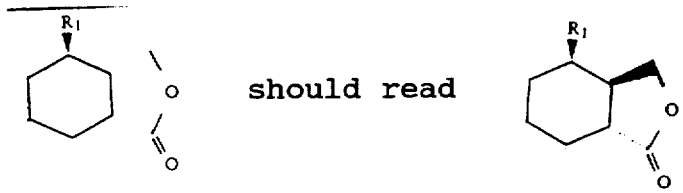

Column 33, TABLE IV, that portion of the formula reading

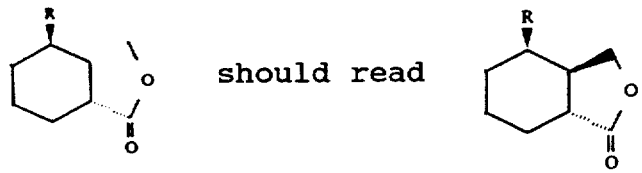

Column 35, lines 4-14, that portion of the formula reading

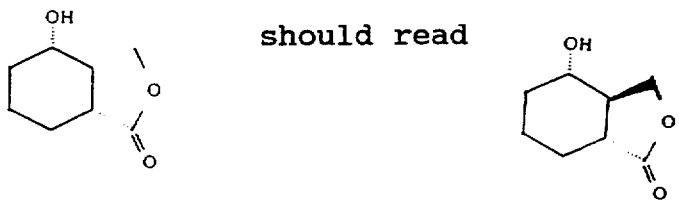

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

Column 36, lines 34-45, that portion of the formula reading

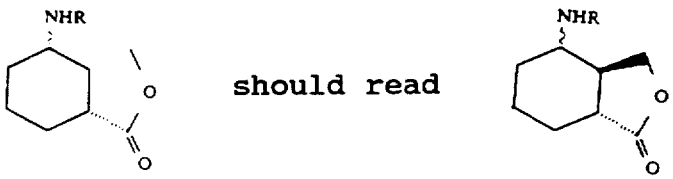

Column 36, lines 52-67, that portion of the formula reading

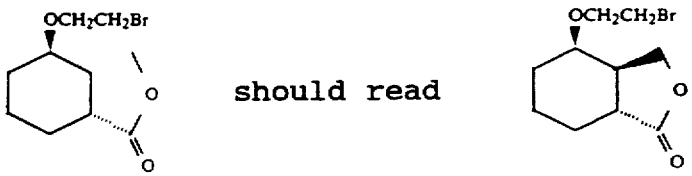

Column 37, lines 4-16, that portion of the formula reading

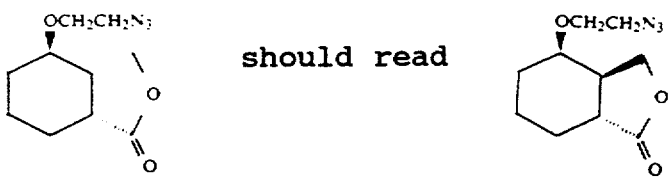

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

Column 37, lines 18-31, that portion of the formula reading

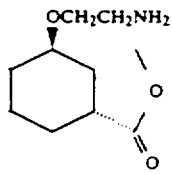   should read   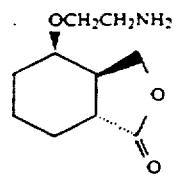

Column 37, lines 36-48, that portion of the formula reading

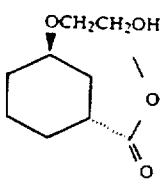   should read   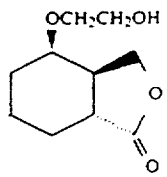

Column 37, lines 53-67, that portion of the formula reading

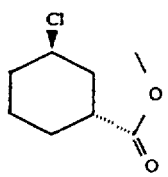   should read   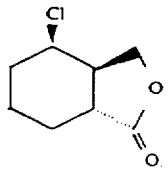

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

Column 38, lines 4-21, that portion of the formula reading

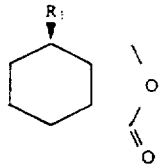   should read   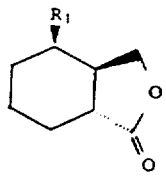

Column 38, lines 27-37, that portion of the formula reading

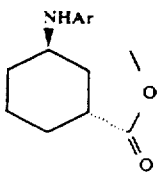   should read   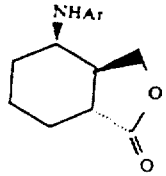

Column 38, lines 42-52, that portion of the formula reading

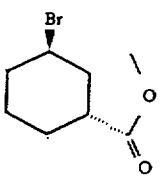   should read   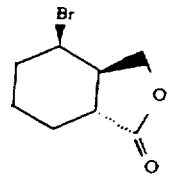

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

Column 38, lines 54-65, that portion of the formula reading

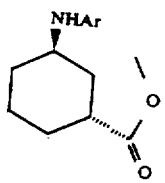   should read   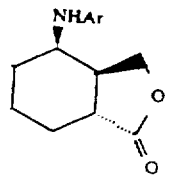

Claim 1, lines 4-15, (col. 39, lines 3-14) that portion of the formula reading

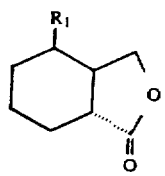   should read   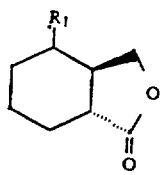

Claim 2, lines 4-15, (col. 39, lines 45-56) that portion of the formula reading

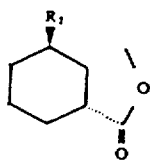   should read   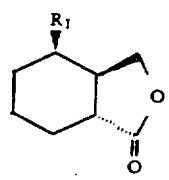

UNITED STATES PATENT AND TRADEMARK OFFICE
CERTIFICATE OF CORRECTION

PATENT NO. : 5,132,322
DATED : July 21, 1992
INVENTOR(S) : LEE, et al.

It is certified that error appears in the above-identified patent and that said Letters Patent is hereby corrected as shown below:

Claim 2, line 17, (col. 39, line 58) replace
"--NHCCH₃HCH₂OH" with -- --NHCH₂CH(CH₃)OH--; and
    lines 17-18, (col. 39, lines 58-59) replace
"--NHCH₂CCH-₃HOH" with -- --NHCH₂CH(CH₃)OH--.

Claim 3, lines 4-13, (col. 40, lines 3-12) that portion of the formula reading

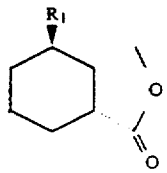   should read   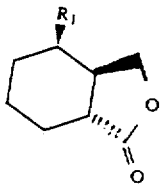

Claim 4, lines 4-16, (col. 40, lines 18-30) that portion of the formula reading

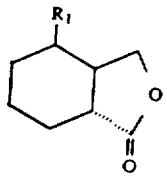   should read   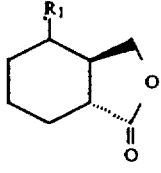

Claim 4, lines 26-31, (col. 40, lines 40-45) that portion of the formula reading

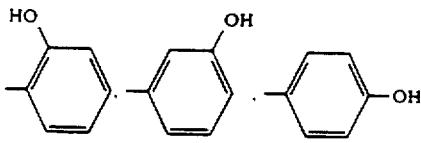   should read   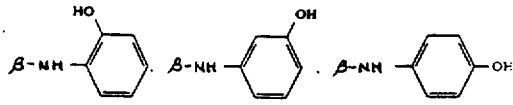

UNITED STATES PATENT AND TRADEMARK OFFICE
CERTIFICATE OF CORRECTION

PATENT NO.  :  5,132,322

DATED       :  July 21, 1992

INVENTOR(S) :  LEE, et al.

It is certified that error appears in the above-identified patent and that said Letters Patent is hereby corrected as shown below:

Claim 6, lines 4-14, (col. 40, lines 57-67) that portion of the formula reading

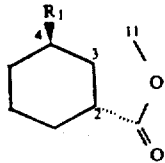   should read   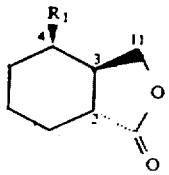

Claim 7, lines 5-15, (col. 41, lines 15-25) that portion of the formula reading

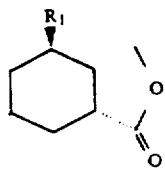   should read   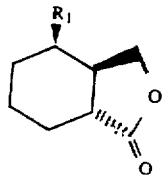

Claim 8, lines 4-13, (col. 42, lines 28-37) that portion of the formula reading

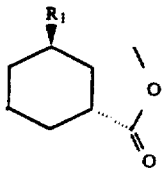   should read   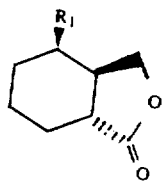

Signed and Sealed this

Sixth Day of December, 1994

Attest:

BRUCE LEHMAN

*Attesting Officer*   *Commissioner of Patents and Trademarks*